(12) United States Patent
Seibel et al.

(10) Patent No.: US 8,840,566 B2
(45) Date of Patent: Sep. 23, 2014

(54) CATHETER WITH IMAGING CAPABILITY ACTS AS GUIDEWIRE FOR CANNULA TOOLS

(75) Inventors: Eric J. Seibel, Seattle, WA (US); Richard S. Johnston, Sammamish, WA (US); Charles David Melville, Issaquah, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 11/695,287

(22) Filed: Apr. 2, 2007

(65) Prior Publication Data

US 2008/0243031 A1    Oct. 2, 2008

(51) Int. Cl.
| A61B 10/00 | (2006.01) |
| A61B 1/00 | (2006.01) |
| A61B 10/02 | (2006.01) |
| A61B 10/04 | (2006.01) |
| A61B 10/06 | (2006.01) |
| A61B 17/32 | (2006.01) |

(52) U.S. Cl.
CPC ............ *A61B 10/02* (2013.01); *A61B 1/00172* (2013.01); *A61B 10/0283* (2013.01); *A61B 2017/320008* (2013.01); *A61B 10/0266* (2013.01); *A61B 10/04* (2013.01); *A61B 10/06* (2013.01); *A61B 1/0008* (2013.01); *A61B 2017/320004* (2013.01)
USPC ............................................ 600/566; 600/176

(58) Field of Classification Search
USPC ................................. 600/566, 176
See application file for complete search history.

(56) References Cited

U.S. PATENT DOCUMENTS

| 4,118,270 A | 10/1978 | Pan et al. .................... 156/659 |
| 4,234,788 A | 11/1980 | Palmer et al. ................ 250/227 |

(Continued)

FOREIGN PATENT DOCUMENTS

| DE | 4428967 | 12/1995 | ............ A61B 17/36 |
| EP | 0 713 672 | 5/1996 | .............. A61B 1/00 |

(Continued)

OTHER PUBLICATIONS

Murakami et al. "A Miniature Confocal Optical Microscope With MEMS Gimbal Scanner" 12th international conference on solid state sensors, actuators, and microsystems Boston 2003. as submitted by applicant.*

(Continued)

*Primary Examiner* — Max Hindenburg
*Assistant Examiner* — Renee Danega
(74) *Attorney, Agent, or Firm* — Wilson Sonsini Goodrich & Rosati

(57) ABSTRACT

A catheter having an imaging device on its distal end serves as a guidewire for cannula tools, enabling the tools to be advanced to a desired site in a patient's body. One exemplary embodiment of such a catheter is a scanning fiber endoscope. The images facilitate navigation through linked body lumens and also enable an operator to view a site where a biopsy sample is to be taken with a cannula tool. Exemplary cannula tools include bristles or sharp points that scrub cells from adjacent tissue, a biopsy needle that can be thrust into tissue, a loop that cuts away tissue, a cutting edge that slices tissue from a site, and forceps. The sample can be carried by a bodily or introduced fluid to a proximal end of the catheter through an annular gap between the catheter and the cannula tool, or the cannula tool can retain the sample.

38 Claims, 16 Drawing Sheets

(56) References Cited

U.S. PATENT DOCUMENTS

| | | | |
|---|---|---|---|
| 4,265,699 A | 5/1981 | Ladany | 156/657 |
| 4,410,235 A | 10/1983 | Klement et al. | 350/96.18 |
| 4,454,547 A | 6/1984 | Yip et al. | 358/293 |
| 4,686,963 A | 8/1987 | Cohen et al. | 128/4 |
| 4,688,555 A | 8/1987 | Wardle | 128/4 |
| 4,695,163 A | 9/1987 | Schachar | 356/369 |
| 4,710,619 A | 12/1987 | Haberl | 250/203 |
| 4,743,283 A | 5/1988 | Borsuk | 65/2 |
| 4,758,222 A | 7/1988 | McCoy | 604/95 |
| 4,762,118 A | 8/1988 | Lia et al. | 128/4 |
| 4,768,513 A | 9/1988 | Suzuki | 128/634 |
| 4,782,228 A | 11/1988 | Westell | 250/236 |
| 4,804,395 A | 2/1989 | Clark et al. | 65/2 |
| 4,824,195 A | 4/1989 | Khoe | 350/96.18 |
| 4,850,364 A | 7/1989 | Leavitt | 128/661.09 |
| 4,928,316 A | 5/1990 | Heritage et al. | 455/600 |
| 4,979,496 A | 12/1990 | Komi | 128/4 |
| 4,983,165 A | 1/1991 | Loiterman | 604/95 |
| 5,037,174 A | 8/1991 | Thompson | 385/33 |
| 5,074,642 A | 12/1991 | Hicks | 385/116 |
| 5,103,497 A | 4/1992 | Hicks | 385/117 |
| 5,172,685 A | 12/1992 | Nudelman | 128/6 |
| 5,209,117 A | 5/1993 | Bennett | 73/517 |
| 5,231,286 A | 7/1993 | Kajimura et al. | 250/234 |
| 5,247,174 A | 9/1993 | Berman | 250/235 |
| 5,272,330 A | 12/1993 | Betzig et al. | 250/216 |
| 5,286,970 A | 2/1994 | Betzig et al. | 250/227.26 |
| 5,305,759 A | 4/1994 | Kaneko et al. | 600/476 |
| 5,321,501 A | 6/1994 | Swanson et al. | 356/345 |
| 5,360,968 A | 11/1994 | Scott | 235/454 |
| 5,381,782 A | 1/1995 | DeLaRama et al. | 128/4 |
| 5,394,500 A | 2/1995 | Marchman | 385/123 |
| 5,405,337 A | 4/1995 | Maynard | 604/281 |
| 5,425,123 A | 6/1995 | Hicks | 385/117 |
| 5,459,803 A | 10/1995 | Yamane et al. | 385/33 |
| 5,480,046 A | 1/1996 | Filas et al. | 216/7 |
| 5,507,725 A | 4/1996 | Savage et al. | 604/95 |
| 5,512,035 A | 4/1996 | Konstorum et al. | 600/146 |
| 5,535,759 A * | 7/1996 | Wilk | 128/898 |
| 5,549,542 A | 8/1996 | Kovalcheck | 600/146 |
| 5,563,969 A | 10/1996 | Honmou | 385/35 |
| 5,570,441 A | 10/1996 | Filas et al. | 385/43 |
| 5,627,922 A | 5/1997 | Kopelman et al. | 385/12 |
| 5,643,175 A | 7/1997 | Adair | 600/133 |
| 5,649,897 A | 7/1997 | Nakamura | 600/111 |
| 5,668,644 A | 9/1997 | Kuroiwa et al. | 358/480 |
| 5,703,979 A | 12/1997 | Filas et al. | 385/43 |
| 5,715,337 A | 2/1998 | Spitzer et al. | 385/4 |
| 5,724,169 A | 3/1998 | LaGasse | 359/173 |
| 5,727,098 A | 3/1998 | Jacobson | 385/31 |
| 5,765,561 A | 6/1998 | Chen et al. | 128/653.1 |
| 5,894,122 A | 4/1999 | Tomita | 250/234 |
| 5,906,620 A | 5/1999 | Nakao et al. | 606/113 |
| 5,919,200 A | 7/1999 | Stambaugh et al. | 606/159 |
| 5,939,709 A | 8/1999 | Ghislain et al. | 250/216 |
| 5,947,905 A * | 9/1999 | Hadjicostis et al. | 600/463 |
| 5,984,860 A | 11/1999 | Shan | 600/116 |
| 5,991,697 A | 11/1999 | Nelson et al. | 702/49 |
| 6,035,229 A | 3/2000 | Silverstein et al. | 600/473 |
| 6,046,720 A | 4/2000 | Melville et al. | 345/108 |
| 6,069,698 A | 5/2000 | Ozawa et al. | 356/345 |
| 6,081,605 A | 6/2000 | Roth et al. | 382/103 |
| 6,091,067 A | 7/2000 | Drobot et al. | 250/234 |
| 6,096,054 A | 8/2000 | Wyzgala et al. | 606/170 |
| 6,097,528 A | 8/2000 | Lebby et al. | 359/251 |
| 6,134,003 A | 10/2000 | Tearney et al. | 356/345 |
| 6,142,957 A * | 11/2000 | Diamond et al. | 600/567 |
| 6,148,095 A | 11/2000 | Prause et al. | 382/131 |
| 6,161,035 A | 12/2000 | Furusawa | 600/476 |
| 6,169,281 B1 | 1/2001 | Chen et al. | 250/234 |
| 6,185,443 B1 | 2/2001 | Crowley | 600/407 |
| 6,191,862 B1 | 2/2001 | Swanson et al. | 356/450 |
| 6,211,904 B1 | 4/2001 | Adair et al. | 348/76 |
| 6,215,437 B1 | 4/2001 | Schurmann et al. | 342/42 |
| 6,240,312 B1 | 5/2001 | Alfano et al. | 600/476 |
| 6,241,657 B1 | 6/2001 | Chen et al. | 600/117 |
| 6,246,914 B1 | 6/2001 | de la Rama et al. | 607/122 |
| 6,289,144 B1 | 9/2001 | Neuschafer et al. | 385/12 |
| 6,294,775 B1 | 9/2001 | Seibel et al. | 250/208.1 |
| 6,327,493 B1 | 12/2001 | Ozawa et al. | 600/476 |
| 6,370,422 B1 | 4/2002 | Richards-Kortum et al. | 600/478 |
| 6,387,119 B2 | 5/2002 | Wolf et al. | 623/1.11 |
| 6,441,359 B1 | 8/2002 | Cozier et al. | 250/216 |
| 6,443,894 B1 | 9/2002 | Sumanaweera et al. | 600/443 |
| 6,461,337 B1 | 10/2002 | Minotti et al. | 604/264 |
| 6,466,687 B1 | 10/2002 | Uppaluri et al. | 382/128 |
| 6,485,413 B1 | 11/2002 | Boppart et al. | 600/160 |
| 6,515,274 B1 | 2/2003 | Moskovits et al. | 250/216 |
| 6,515,781 B2 | 2/2003 | Lewis et al. | 359/204 |
| 6,525,310 B2 | 2/2003 | Dunfield | 250/235 |
| 6,545,260 B1 | 4/2003 | Katashiro et al. | 250/227.26 |
| 6,546,271 B1 | 4/2003 | Reisfeld | 600/407 |
| 6,549,801 B1 | 4/2003 | Chen et al. | 600/425 |
| 6,550,918 B1 | 4/2003 | Agostinelli et al. | 353/7 |
| 6,563,105 B2 | 5/2003 | Seibel et al. | 250/208.1 |
| 6,563,998 B1 | 5/2003 | Farah et al. | 385/131 |
| 6,564,087 B1 | 5/2003 | Pitris et al. | 600/478 |
| 6,564,089 B2 | 5/2003 | Izatt et al. | 600/478 |
| 6,612,980 B2 | 9/2003 | Chen et al. | 600/117 |
| 6,615,072 B1 | 9/2003 | Izatt et al. | 600/478 |
| 6,678,541 B1 | 1/2004 | Durkin et al. | 600/310 |
| 6,685,718 B1 | 2/2004 | Wyzgala et al. | 606/170 |
| 6,687,010 B1 | 2/2004 | Horii et al. | 356/479 |
| 6,689,064 B2 | 2/2004 | Hager et al. | 600/454 |
| 6,690,963 B2 | 2/2004 | Ben-Haim et al. | 600/424 |
| 6,694,983 B2 | 2/2004 | Wolf et al. | 128/898 |
| 6,735,463 B2 | 5/2004 | Izatt et al. | 600/476 |
| 6,755,532 B1 | 6/2004 | Cobb | 353/7 |
| 6,773,394 B2 | 8/2004 | Taniguchi et al. | 600/117 |
| 6,779,892 B2 | 8/2004 | Agostinelli et al. | 353/7 |
| 6,785,571 B2 | 8/2004 | Glossop | 600/424 |
| 6,788,967 B2 | 9/2004 | Ben-Haim et al. | 600/424 |
| 6,818,001 B2 | 11/2004 | Wulfman et al. | 606/159 |
| 6,826,342 B1 | 11/2004 | Bise et al. | 385/125 |
| 6,832,984 B2 | 12/2004 | Stelzer et al. | 604/93.01 |
| 6,836,560 B2 | 12/2004 | Emery | 382/145 |
| 6,839,586 B2 | 1/2005 | Webb | 600/478 |
| 6,845,190 B1 | 1/2005 | Smithwick et al. | 385/25 |
| 6,856,712 B2 | 2/2005 | Fauver et al. | 385/12 |
| 6,858,005 B2 | 2/2005 | Ohline et al. | 600/141 |
| 6,872,433 B2 | 3/2005 | Seward et al. | 428/36.9 |
| 6,882,429 B1 | 4/2005 | Weitekamp et al. | 356/482 |
| 6,889,175 B2 | 5/2005 | Green | 702/190 |
| 6,892,090 B2 | 5/2005 | Verard et al. | 600/424 |
| 6,895,270 B2 | 5/2005 | Ostrovsky | 600/476 |
| 6,902,528 B1 | 6/2005 | Garibaldi et al. | 600/118 |
| 6,932,829 B2 | 8/2005 | Majercak | 606/198 |
| 7,004,173 B2 * | 2/2006 | Sparks et al. | 128/898 |
| 7,023,558 B2 | 4/2006 | Fee et al. | 356/489 |
| 7,038,191 B2 | 5/2006 | Kare et al. | 250/227.11 |
| 7,072,046 B2 | 7/2006 | Xie et al. | 356/479 |
| 7,158,234 B2 | 1/2007 | Uchiyama et al. | 356/479 |
| 7,170,610 B2 | 1/2007 | Knuttel | 356/456 |
| 7,179,220 B2 | 2/2007 | Kukuk | 600/118 |
| 7,189,961 B2 | 3/2007 | Johnston et al. | 250/234 |
| 7,252,674 B2 * | 8/2007 | Wyzgala et al. | 606/170 |
| 7,324,211 B2 | 1/2008 | Tsujita | 356/497 |
| 7,349,098 B2 | 3/2008 | Li et al. | 356/479 |
| 7,366,376 B2 | 4/2008 | Shishkov et al. | 385/35 |
| 7,404,929 B2 | 7/2008 | Fulghum, Jr. | 422/82.05 |
| 7,447,408 B2 | 11/2008 | Bouma et al. | 385/123 |
| 7,515,274 B2 | 4/2009 | Gelikonov et al. | 356/479 |
| 7,615,005 B2 | 11/2009 | Stefanchik et al. | 600/106 |
| 7,616,986 B2 | 11/2009 | Seibel et al. | 600/476 |
| 7,747,312 B2 | 6/2010 | Barrick et al. | 600/426 |
| 7,783,337 B2 | 8/2010 | Feldman et al. | 600/160 |
| 2001/0030744 A1 | 10/2001 | Chang et al. | 356/73 |
| 2001/0055462 A1 * | 12/2001 | Seibel | 385/147 |
| 2002/0071625 A1 | 6/2002 | Bartholomew et al. | 385/12 |
| 2003/0009189 A1 | 1/2003 | Gilson et al. | 606/200 |
| 2003/0032878 A1 | 2/2003 | Shahidi | 600/429 |
| 2003/0045778 A1 | 3/2003 | Ohline et al. | 600/114 |
| 2003/0055317 A1 | 3/2003 | Taniguchi et al. | 600/117 |
| 2003/0103199 A1 | 6/2003 | Jung et al. | 356/73 |

(56) References Cited

U.S. PATENT DOCUMENTS

| | | | |
|---|---|---|---|
| 2003/0103665 A1 | 6/2003 | Uppaluri et al. | 382/131 |
| 2003/0142934 A1 | 7/2003 | Pan et al. | 385/116 |
| 2003/0160721 A1 | 8/2003 | Gilboa et al. | 342/450 |
| 2003/0179428 A1 | 9/2003 | Suzuki et al. | 359/204 |
| 2003/0208107 A1 | 11/2003 | Refael | 600/300 |
| 2003/0208134 A1 | 11/2003 | Secrest et al. | 600/562 |
| 2003/0216639 A1 | 11/2003 | Gilboa et al. | 600/424 |
| 2003/0220749 A1 | 11/2003 | Chen et al. | 702/31 |
| 2003/0236564 A1 | 12/2003 | Majercak | 623/1.11 |
| 2004/0015049 A1 | 1/2004 | Zarr | 600/101 |
| 2004/0015053 A1 | 1/2004 | Bieger et al. | 600/117 |
| 2004/0033006 A1 | 2/2004 | Farah | 385/14 |
| 2004/0061072 A1 | 4/2004 | Gu et al. | 250/458.1 |
| 2004/0118415 A1 | 6/2004 | Hall et al. | 128/898 |
| 2004/0147827 A1 | 7/2004 | Bowe | 600/374 |
| 2004/0176683 A1 | 9/2004 | Whitin et al. | 600/424 |
| 2004/0181148 A1 | 9/2004 | Uchiyama et al. | 600/425 |
| 2004/0199052 A1 | 10/2004 | Banik et al. | 600/142 |
| 2004/0243227 A1 | 12/2004 | Starksen et al. | 623/2.11 |
| 2004/0249267 A1 | 12/2004 | Gilboa | 600/204 |
| 2004/0260199 A1* | 12/2004 | Hardia et al. | 600/566 |
| 2005/0020878 A1 | 1/2005 | Ohnishi et al. | 600/117 |
| 2005/0020914 A1* | 1/2005 | Amundson et al. | 600/431 |
| 2005/0020926 A1* | 1/2005 | Wiklof et al. | 600/476 |
| 2005/0036150 A1 | 2/2005 | Izatt et al. | 356/479 |
| 2005/0054931 A1 | 3/2005 | Clark | 600/453 |
| 2005/0065433 A1 | 3/2005 | Anderson | 600/424 |
| 2005/0085693 A1 | 4/2005 | Belson et al. | 600/146 |
| 2005/0111009 A1 | 5/2005 | Keightley et al. | 356/602 |
| 2005/0168751 A1 | 8/2005 | Horii et al. | 356/479 |
| 2005/0171438 A1 | 8/2005 | Chen et al. | 600/476 |
| 2005/0171520 A1* | 8/2005 | Farr et al. | 606/15 |
| 2005/0171592 A1 | 8/2005 | Majercak | 623/1.11 |
| 2005/0183733 A1 | 8/2005 | Kawano et al. | 128/899 |
| 2005/0206774 A1 | 9/2005 | Tsujimoto | 348/345 |
| 2005/0215854 A1 | 9/2005 | Ozaki et al. | 600/109 |
| 2005/0215911 A1 | 9/2005 | Alfano et al. | 600/476 |
| 2005/0228290 A1 | 10/2005 | Borovsky et al. | 600/466 |
| 2005/0234345 A1* | 10/2005 | Yang | 600/476 |
| 2005/0250983 A1 | 11/2005 | Tremaglio et al. | 600/101 |
| 2005/0272975 A1 | 12/2005 | McWeeney et al. | 600/113 |
| 2006/0015126 A1* | 1/2006 | Sher | 606/159 |
| 2006/0030753 A1 | 2/2006 | Boutillette et al. | 600/146 |
| 2006/0052662 A1 | 3/2006 | Kress | 600/123 |
| 2006/0100480 A1 | 5/2006 | Ewers et al. | 600/114 |
| 2006/0106317 A1 | 5/2006 | McConnell et al. | 600/476 |
| 2006/0126064 A1 | 6/2006 | Bambot et al. | 356/337 |
| 2006/0149134 A1 | 7/2006 | Soper et al. | 600/182 |
| 2006/0149163 A1* | 7/2006 | Hibner et al. | 600/566 |
| 2006/0187462 A1 | 8/2006 | Srinivasan et al. | 356/479 |
| 2006/0195014 A1 | 8/2006 | Seibel et al. | 600/102 |
| 2006/0202115 A1 | 9/2006 | Lizotte et al. | 250/234 |
| 2006/0235273 A1* | 10/2006 | Moriyama et al. | 600/113 |
| 2006/0241495 A1 | 10/2006 | Kurtz | 600/476 |
| 2006/0252993 A1 | 11/2006 | Freed et al. | 600/146 |
| 2007/0038119 A1 | 2/2007 | Chen et al. | 600/476 |
| 2007/0066983 A1 | 3/2007 | Maschke | 606/159 |
| 2007/0088219 A1 | 4/2007 | Xie et al. | 600/473 |
| 2007/0093703 A1 | 4/2007 | Sievert et al. | 600/343 |
| 2007/0129601 A1 | 6/2007 | Johnston et al. | 600/109 |
| 2007/0213618 A1 | 9/2007 | Li et al. | 600/476 |
| 2007/0270650 A1 | 11/2007 | Eno et al. | 600/145 |
| 2008/0004491 A1 | 1/2008 | Karasawa | 600/101 |
| 2008/0221388 A1 | 9/2008 | Seibel et al. | 600/109 |

FOREIGN PATENT DOCUMENTS

| | | | | |
|---|---|---|---|---|
| EP | 0 520 388 | 9/1996 | | B41J 2/455 |
| EP | 1 077 360 | 2/2001 | | G01B 9/02 |
| EP | 1 088 515 | 4/2001 | | A61B 5/06 |
| EP | 1 142 529 | 10/2001 | | A61B 1/00 |
| EP | 0 712 032 | 12/2001 | | G03B 35/08 |
| EP | 1 310 206 | 5/2003 | | A61B 1/015 |
| EP | 1 421 913 | 5/2004 | | A61B 19/00 |
| EP | 0 910 284 | 1/2007 | | A61B 10/00 |
| EP | 1 063 921 | 2/2007 | | A61B 10/00 |
| JP | 05-154154 | 6/1993 | | A61B 10/00 |
| JP | 06-511312 | 12/1994 | | G01B 9/02 |
| JP | 2001174744 | 6/2001 | | G02B 23/24 |
| WO | WO 93/20742 | 10/1993 | | A61B 1/06 |
| WO | WO 96/02184 | 2/1996 | | A61B 5/00 |
| WO | WO 98/38907 | 9/1998 | | A61B 5/00 |
| WO | WO 98/43530 | 10/1998 | | A61B 1/00 |
| WO | WO 99/04301 | 1/1999 | | G02B 21/00 |
| WO | WO 01/97902 | 12/2001 | | |
| WO | WO 2005/024496 | 3/2005 | | |

OTHER PUBLICATIONS

Yelin, D., I. Rizvi, W.M. White, J.T. Motz, T. Hasan, B.E. Bouma, and G.J. Tearney. "Three-dimensional miniature endoscopy" *Nature* vol. 443, Oct. 19, 2006, p. 765.

Supplemental information for above article from *Nature*, Oct. 19, 2006. www.nature.com/nature/journal/v443/n7113/extref/443765a-s2.doc.

Martinez, O.E., "3000 Times Grating Compressor with Positive Group-Velocity Dispersion—Application to Fiber Compensation in 1.3-1.6 µm Region." *IEEE Journal of Quantum Electronics* vol. 23: 59-64, 1987.

Mori et al., "A Method for Tracking camera motion of real endoscope by using virtual endoscopy system." *Proceedings of SPIE*: 1-12, 2000. <www.http://www.toriwaki.nuie.nagoya-u.ac.jp>12pp. 1-12.

Morofke et al., "Wide dynamic range detection of bidirectional flow in Doppler optical coherence tomography using a two-dimensional Kasai estimatior." *Optics Letters*, vol. 32, No. 3: 253-255, Feb. 1, 2007.

Murakami et al., "A Miniature Confocal Optical Microscope With Mems Gimbal Scanner." *The 12th International Conference on Solid State Sensors, Actuators and Microsystems* Boston: 587-590, Jun. 8-12, 2003.

Myaing et al., "Enhanced two-photon biosensign with double-clad photonic crystal fibers," *Optics Letters*, vol. 28, No. 14: 1224-1226, 2003.

Ohmi et al., "Quasi In-Focus Optical Coherence Tomography." *Japanese Journal of Applied Physics* vol. 43, No. 2: 845-849, 2004.

Oikawa et al., "Intra-operative Guidance with Real-time Information of Open MRI and Manipulators Using Coordinate-Integration Module." *Proceedings of SPIE*, vol. 5029: 653-660, 2003.

Pagoulatos et al., "Image-based Registration of Ultrasound and Magnetic Resonance Images: A Preliminary Study." *Proceedings of SPIE*, vol. 3976: 156-164, 2000.

Patterson et al., "Applications of time-resolved light scattering measurements to photodynamic therapy dosimetry." *SPIE* vol. 1203, Photodynamic Therapy: Mechanism II: 62-75, 1990.

Pyhtila et al., "Determining nuclear morphology using an improved angle-resolved low coherence interferometry system." *Optics Express*, vol. 11, No. 25: 3473-3484, Dec. 15, 2003.

Pyhtila et al., "Fourier-domain angle-resolved low coherence interferometry through an endoscopic fiber bundle for light-scattering spectroscopy." *Optics Letters*, vol. 31, No. 6: 772-774, Dec. 1, 2005.

Pyhtila et al., "Rapid, depth-resolved light scattering measurements using Fourier domain, angle-resolved low coherence interferometry." *Optical Society of America*: 6pp, 2004.

Podoleanu et al., "Three dimensional OCT images from retina and skin." *Optics Express* vol. 7, No. 9: 292-298, 2000.

Qi et al., "Dynamic focus control in high-speed optical coherence tomography based on a microelectromechanical mirror." *Optics Communications* vol. 232: 123-128, 2004.

Russo et al., "Lens-ended Fibers for Medical Applications: A New Fabrication Technique." *Appl. Opt.* vol. 23, No. 19: 3277-3283, Oct. 1, 1984.

Sasaki et al., "Scanning Near-Field Optical Microscope using Cantilever Integrated with Light Emitting Diode, Waveguide, Aperture, and Photodiode." Optical MEMS 2000 Invited Speakers: Advance Program, Sponsored by IEEE Lasers and Electro-Optics Society: 16pp, 2000. Available at <http://www.ieee.org/organizations/society/leos/LEOSCONF/MEMS/omspeak.html.>.

(56) References Cited

OTHER PUBLICATIONS

Schmitt et al., "An optical coherence microscope with enhanced resolving power in thick tissue." *Optics Communications* 142: 203-207, 1997.

Schwartz et al., "Electromagnetic Navigation during Flexible Bronchoscopy." *Interventional Pulmonology: Respiration*, vol. 70: 516-522, 2003.

Seibel et al., "Unique Features of Optical Scanning, Single Fiber Endoscopy." *Lasers in Surgery and Medicine* vol. 30: 177-183, 2002.

Shahidi et al., "Implementation, Calibration and Accuracy Testing of an Image-Enhanced Endoscopy System." *IEEE Transactions on Medical Imaging*, vol. 21, No. 12: 1524-1535, 2002.

Shinagawa et al., "CT-Guided Transbronchial Biopsy Using an Ultrathin Bronchoscopic Navigation." *Chest*, vol. 125, No. 3: 1138-1143, 2003.

Shiraishi et al., "Spot Size Reducer for Standard Single-Mode Fibers Utilizing a Graded-Index Fiber Tip." *ECOC 97*: 50-53, Sep. 22-25, 1997.

Shoji et al., "Camera motion tracking of real endoscope by using virtual endoscopy system and texture information." *Proceedings of SPIE*, vol. 4321: 122-133, 2001.

Skala et al., "Multiphoton Microscopy of Endogenous Fluorescence Differentiates Normal, Precancerous, and Cancerous Squamous Epithelial Tissues." *Cancer Research* vol. 65, No. 4: 1180-1186, Feb. 15, 2005. Available at <www.aacrjournals.org>.

Smithwick et al., "Modeling and Control of the Resonant Fiber Scanner for Laser Scanning Display or Acquisition." *SID 03 Digest*: 1455-1457, 2003.

Solomon et al., "Three-dimensional CT-Guided Bronchoscopy With a Real-Time Electromagnetic Position Sensor," "A Comparison of Two Image Registration Methods." *Chest*, vol. 118, No. 6: 1783-1787, 2000.

Srivastava, S., "Computer-Aided Identification of Ovarian Cancer in Confocal Microendoscope Images," Department of Electrical and Computer Engineering, University of Arizona Graduate School, Thesis: 213pp, 2004.

Tearney et al., "Determination of the Refractive-Index of Highly Scattering Human Tissue by Optical Coherence Tomography." *Optics Letters*, vol. 20, No. 21: 2258-2260, 1995.

Tsai et al., "All-Optical Histology Using Ultrashort Laser Pulses." *Neuron* Cell Press, vol. 39: 27-41, Jul. 3, 2003.

Vakoc et al., "Comprehensive esophageal microscopy by using optical frequency-domain imaging (with video)." *Gastrointestinal Endoscopy*, vol. 65, No. 6: 898-905, 2007.

Wang et al., "Deep Reactive Ion Etching of Silicon Using an Aluminum Etching Mask." *Proceedings of SPIE*, vol. 4876: 633-640, 2003.

Wilson et al., "Optical Reflectance and Transmittance of Tissues: Principles and Applications." *IEEE Journal of Quantum Electronics*, vol. 26, No. 12: 2186-2199, Dec. 1990.

Xu et al., "3D Motion Tracking of pulmonary lesions using CT fluoroscopy images for robotically assisted lung biopsy." *Proceedings of SPIE*, vol. 5367: 394-402, 2004.

Yamada et al., "Characteristics of a Hemispherical Microlens for Coupling Between a Semiconductor Laser and Single-Mode Fiber." *IEEE J. Quant. Electron*, vol. QE-16, No. 10: 1067-1072, Oct. 1980.

Yamamoto et al., "Total enteroscopy with a nonsurgical steerable double-balloon method." *Gastrointestinal Endoscopy* vol. 53, No. 2: 216-220, Feb. 2001. Abstract only.

Yang et al., "High speed, wide velocity dynamic range Doppler optical coherence tomography (Part I): System design, signal processing, and performance." *Optics Express*, vol. 11, No. 7: 794-809, Apr. 7, 2003.

Yang et al., "Micromachined array tip for multifocus fiber-based optical coherence tomography." *Optics Letters*, vol. 29, No. 15: 1754-1756, 2004.

Yelin et al., "Double-clad fiber for endoscopy." *Optics Letters*, vol. 29, No. 20: 2408-2410, Oct. 15, 2004.

Yoon et al., "Analysis of Electro Active Polymer Bending: A Component in a Low Cost Ultrathin Scanning Endoscope." *Sensors and Actuators A—Physical*: pp. 1-26, Submitted Jan. 13, 2006, Published Jul. 2006.

Yun et al., "Comprehensive volumetric optical microscopy in vivo." *Nature Medicine* vol. 12, No. 12: 1429-1433, Dec. 2006.

Yun et al., "Motion artifacts in optical coherence tomography with frequency-domain ranging." *Optics Express* vol. 12, No. 13: 2977-2998, Jun. 28, 2004.

Zhang et al., "In vivo blood flow imaging by a swept laser source based Fourier domain optical Doppler tomography." *Optics Express* vol. 13, No. 19: 7449-7457, Sep. 19, 2005.

Zipfel et al., "Live tissue intrinsic emission microscopy using multiphoton-excited native fluorescence and second harmonic generation." *PNAS* vol. 100, No. 12: 7075-7080, Jun. 10, 2003. Available at <www.pnas.org/cgi/doi/10.1073/pnas.0832308100>.

n.a., "Given® Diagnostic System." The Platform for PillCam™Endoscopy Given Imaging Ltd.: 4pp, 2001-2004. <http:www.givenimaging.com>.

n.a., "NASA-Inspired Shape-Sensing Fibers Enable Minimally Invasive Surgery." NASA Tech Briefs vol. 32, No. 2: 12, 14, Feb. 2008.

n.a., "NANO™ SU-8 2000 Negative Tone Photoresist Formulations 2002-2025." Micro-Chem: 5pp, © 2001.

Barhoum et al., "Optical modeling of an ultrathin scanning fiber endoscope, a preliminary study of confocal versus non-confocal detection." *Optics Express*, vol. 13, No. 19: 7548-7562, Sep. 19, 2005.

Barnard et al., "Mode Transforming Properties of Tapered Single-mode Fiber Microlens." *Appl. Opt.* vol. 32, No. 12: 2090-2094, Apr. 20, 1993.

Barnard et al., "Single-mode Fiber Microlens with Controllable Spot Size." *Appl. Opt.* vol. 30, No. 15: 1958-1962, May 20, 1991.

Bird et al., "Two-photon fluorescence endoscopy with a micro-optic scanning head." *Optics Letters*, vol. 28, No. 17: 1552-1554, 2003.

Borreman et al., "Fabrication of Polymeric Multimode Waveguides and Devices in SU-8 Photoresist Using Selective Polymerization." *Proceedings Symposium IEEE/LEOS* Benelux Chapter, Amsterdam: pp. 83-86, 2002.

Brown et al., "Recognising Panoramas." *Proceedings of the Ninth IEEE International Conference on Computer Vision* 8pp., Apr. 2003.

Brunetaud et al., "Lasers in Digestive Endoscopy." *Journal of Biomedical Optics* vol. 2, No. 1: 42-52, Jan. 1997.

Chen et al., "Dispersion management up to the third order for real-time optical coherence tomography involving a phase or frequency modulator." *Optics Express* vol. 12, No. 24: 5968-5978, 2004.

Chen et al., "Optical Doppler tomographic imaging of fluid flow velocity in highly scattering media." *Optics Letters*, vol. 22, No. 1: 64-66, 1997.

Clark et al., "Fiber delivery of femtosecond pulses from a Ti:sapphire laser." *Optics Letters*, vol. 26, No. 17: 1320-1322, 2001.

Deschamps et al., "Automatic construction of minimal paths in 3D images: An application to virtual endoscopy." *CARS'99—H. U. Lemke, M.W. Vannier, K. Inamura & A.G. Fannan (Editors) Elsevier Science B.V.*: 151-155, 1999.

Dickensheets et al., "A Scanned Optical Fiber Confocal Microscope." *Three-Dimensional Microscopy* SPIE vol. 2184: 39-47, 1994.

Dickensheets et al., "Micromachined scanning confocal optical microscope." *Optics Letters*, vol. 21, No. 10: 764-766, May 15, 1996.

Drexler et al., "In vivo ultrahigh-resolution optical coherence tomography." *Optics Letters*, vol. 24, No. 17: 1221-1223, 1999.

Finci et al., "Tandem balloon catheter for coronary angioplasty." *Catheter Cardiovascular Diagnosis* vol. 12, No. 6: 421-425, 1986. 2pp Abstract.

Flusberg et al., "In vivo brain imaging using a portable 3.9 gram two-photon fluorescence microendoscope." *Optics Letters*, vol. 30, No. 17: 2272-2274. 2005.

Fu et al., "Nonlinear optical microscopy based on double-clad photonic crystal fibers." *Optics Express* vol. 13, No. 14: 5528-5534+supplemental page, 2005.

(56) References Cited

OTHER PUBLICATIONS

Göbel et al., "Miniaturized two-photon microscope based on a flexible coherent fiber bundle and a gradient-index lens objective." *Optics Letters*, vol. 29, No. 21: 2521-2523, 2004.

Helmchen et al., "A Miniature Head-Mounted Two-Photon Microscope: High Resolution Brain Imaging in Freely Moving Animals." *Neuron* vol. 31: 903-912, Sep. 27, 2001.

Herline et al., "Surface Registration for Use in Interactive, Image-Guided Liver Surgery." *Computer Aided Surgery*, vol. 5: 11-17, 1999.

Higgins et al., "Integrated Bronchoscopic Video Tracking and 3D CT Registration for Virtual Bronchoscopy." *Medical Imaging* 2003, vol. 5031: 80-89, 2003.

Huang et al., "Optical Coherence Tomography." *Science* vol. 254, Issue 5035: 1178-1181, 1991.

Huber et al., "Amplified, frequency swept lasers for frequency domain reflectometry and OCT imaging: design and scaling principles." *Optics Express* vol. 13, No. 9: 3513-3528, May 2, 2005.

Jung et al., "Multiphoton endoscopy." Optics Letters, vol. 28, No. 11: 902-904, 2003.

Kiesslich et al., "Diagnosing *Helicobacter pylori* In Vivo by Confocal Laser Endoscopy." *Gastroenterology* vol. 128: 2119-2123, 2005.

Kiraly et al., "Three-Dimensional Path Planning for Virtual Bronchoscopy." *IEEE Transactions on Medical Imaging*, vol. 23, No. 9: 1365-1379, Sep. 2004.

Lee et al., "Microlenses on the End of Single-mode Optical Fibers for Laser Applications." *Appl. Opt.* vol. 24, No. 19: 3134-3139, Oct. 1, 1985.

Lewis et al., "Scanned beam medical imager." *MOEMS Display and Imaging System II*, edited by Hakan Urey, David L. Dickensheets, Proceedings of SPIE, Bellingham, WA, vol. 5348: 40-51, 2004.

Lexer et al., "Dynamic coherent focus OCT with depth-independent transversal resolution." *Journal of Modern Optics* vol. 46, No. 3: 541-553, 1999.

Li et al., "Optical Coherence Tomography: Advanced Technology for the Endoscopic Imaging of Barrett's Esophagus" *Endoscopy*, vol. 32, No. 12: 921-930, 2000.

Liu et al., "3D Navigation for Endoscope by Magnetic Field." *Proceedings of SPIE*, vol. 4556 25-28, 2001.

Liu et al., "Rapid-scanning forward-imaging miniature endoscope for real-time optical coherence tomography." *Optics Letters*, vol. 29, No. 15: 1763-1765, 2004.

\* cited by examiner

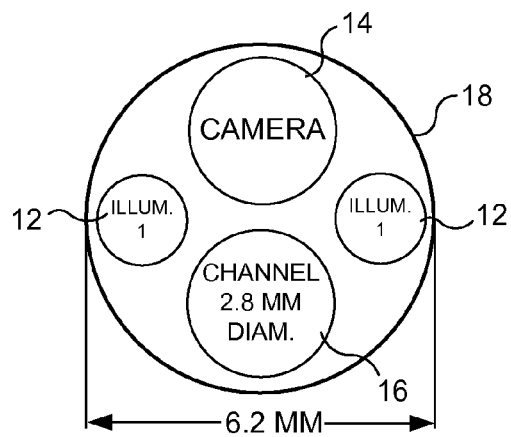
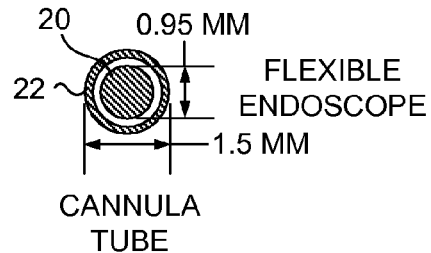
FIG. 1A (PRIOR ART)
FIG. 1B
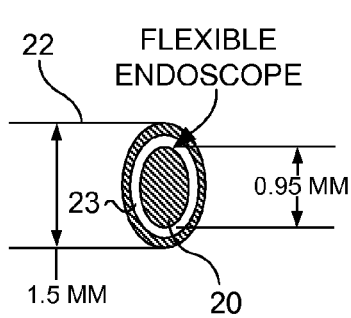
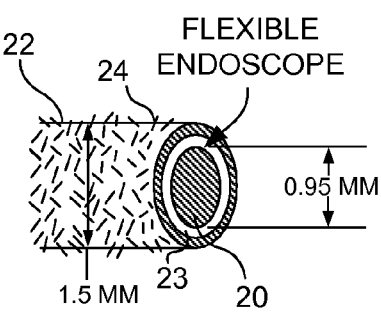
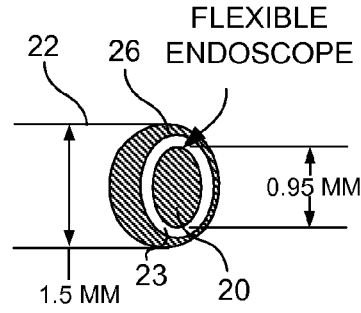
FIG. 2A   FIG. 2B   FIG. 2C
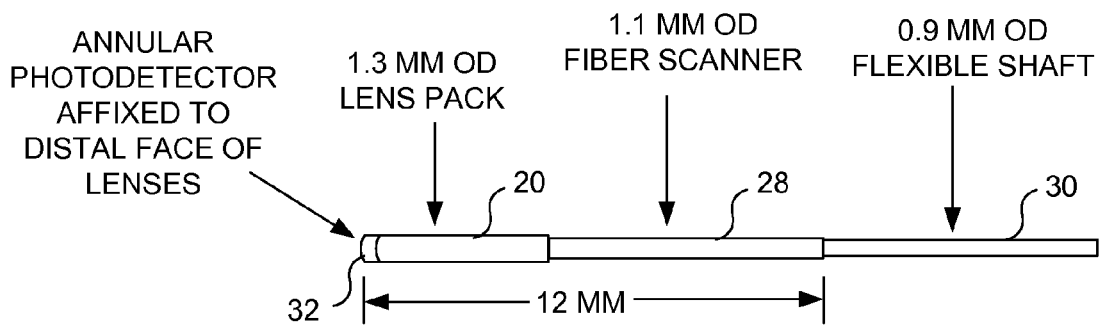
FIG. 3

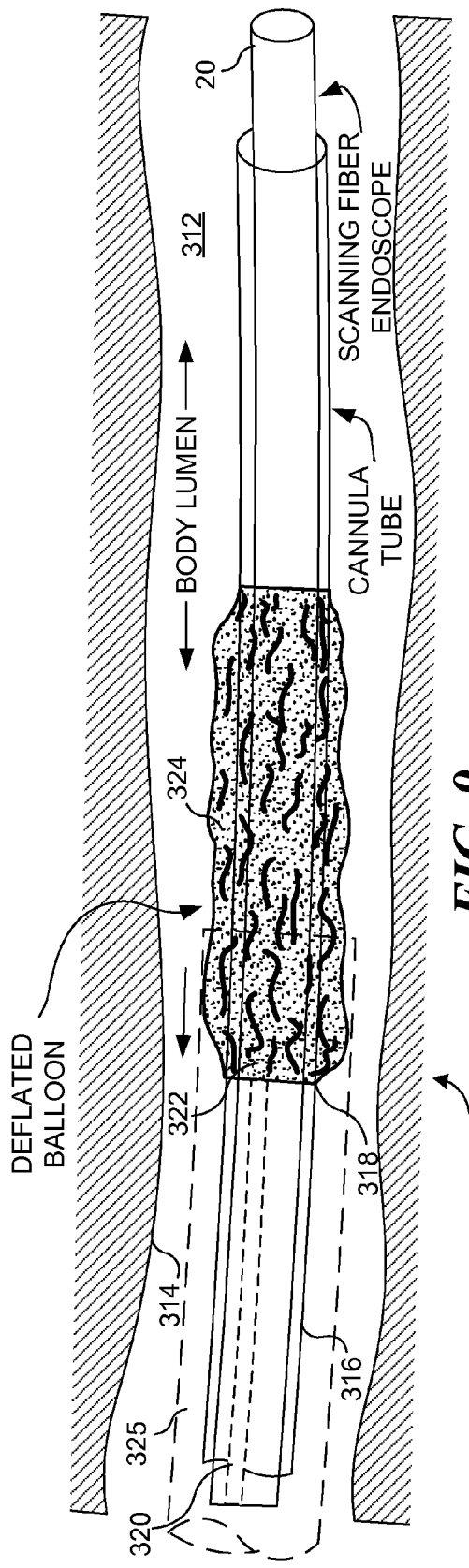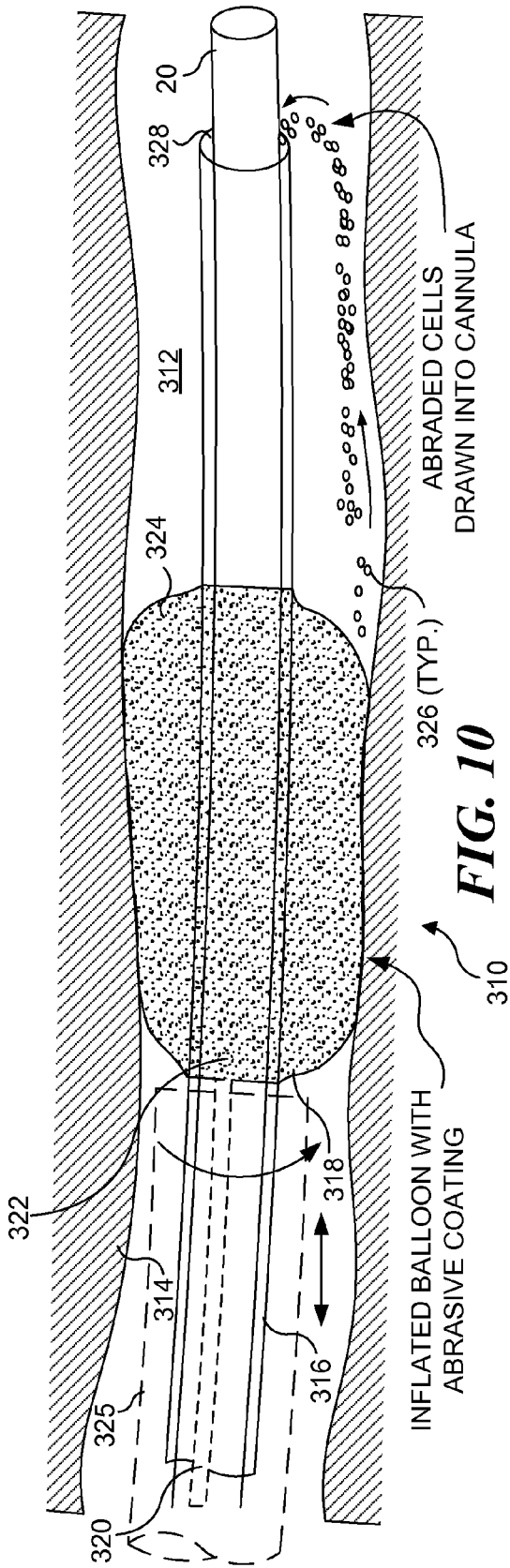

CATHETER WITH IMAGING CAPABILITY ACTS AS GUIDEWIRE FOR CANNULA TOOLS

GOVERNMENT RIGHTS

This invention was made with government support under Grant No. CA094303 awarded by the National Institutes of Health (NIH). The government has certain rights to this invention.

BACKGROUND

A cannula is a hollow flexible tube used in medicine to introduce or open a lumen or to insert medical devices and can be introduced into the human body over a guidewire. Typically this guidewire is a highly-flexible metal coiled wire less than 0.5 mm in diameter and is used extensively in cardiovascular medicine. A catheter has very low flexural rigidity but is able to be pushed from the vein in the leg all the way through the heart. A guidewire can be inserted into the body of a patient in a generally conventional manner and advanced to a desired location where a biopsy of cells and tissue is to be taken. The process of advancing the guidewire can be done purely by exercising the touch and feel of an experienced physician, or can be carried out with visualization technologies, such as fluoroscopy, X-ray or computed tomography (CT) imaging, magnetic resonance imaging (MRI), ultrasound imaging, optical tomography, etc. Clearly, it would be desirable to advance a device that serves as a guidewire by imaging the lumen in the body of a patient through which the device is being advanced.

Catheters with cannula tools that are introduced into a patient's body by means of slipping the catheter with its cannula tools over a guidewire that has previously been maneuvered to a desired location in the body are well developed for cardiovascular applications. In these applications, the task of taking a biopsy for disease diagnosis was not required, so tools for cell sampling have not previously been developed. In contrast, one of the primary purposes of endoscopy and bronchoscopy is disease diagnosis, which often requires taking cell samples and tissue biopsies. It is likely that appropriate tools for taking cell and tissue samples will be useful in the endoscopy and bronchoscopy fields, along with urology and other medical fields that require cell sampling for disease diagnosis. It would clearly be desirable to develop a variety of different types of guidewire-based tools for use in collecting samples from an internal site in a patient's body for cytopathological diagnosis, so that these tools can be advanced over a guidewire that has imaging capability.

After a guidewire has been inserted and advanced to a desired site, it would further be desirable to introduce a multifunction tool over the guidewire as a cannula, or otherwise couple the tool to the guidewire so that it can be advanced to the site over the guidewire and be employed to obtain a biopsy sample at the site. It would also be desirable to develop multifunctional cannula tools that can be employed to carry out more than one function, for example, dislodging cells and tissue, and then capturing and withdrawing the cells and tissue for diagnostic evaluation, to detect disease by applying conventional cytological and pathological procedures.

An endoscope can be made that has only a single optical fiber, for example, 0.1 to 0.3 mm in diameter. Typically, optical fibers made from fused silica, silicon-dioxide, or quartz have the ability to withstand compressive forces and can be used in a way similar to a catheter guidewire, since the distal tip can be steered, e.g., by bending it as it is advanced through a body lumen. Accordingly, it would be desirable to provide a "guidewire with eyes" for introducing cannula tools to a treatment site within a patient's body. Such a device should have many more uses than as a simple guidewire or catheter, since the ability to image as the device is being advanced (and while it is being withdrawn) through a lumen would enable a medical practitioner to introduce the cannula tools to a desired site without the need for external imaging. Such a device would enable cannula tools to be introduced for many different medical applications, and to be used more effectively at a desired site by providing a visual image showing the medical practitioner what is occurring as the cannula tools are being used.

SUMMARY

As described below, a number of advantages arise from using an ultrathin and flexible catheter having an imaging device, as a guidewire for a cannula tool. For example, both a hollow cell sampling tool (i.e., a cannula tool) can be used concurrently with such a catheter having a small overall diameter by simply threading the cell sampling tool over the catheter and advancing it with the distal end of the catheter or sliding it distally along the shaft of the catheter once the distal end of the catheter (with the imaging device) has been positioned at a desired site. A much larger and non-circular cross-sectional shape would be required if the two functions were implemented side-by-side in separate channels, which is typical of the approach currently used in flexible endoscopy. While not intended to be considered limiting, an initial exemplary embodiment of a catheter with imaging capability described herein as "scanning fiber endoscope" has been developed and is ideally suited to serve as a guidewire with eyes for cannula tools. However, it should be stressed that other types of imaging devices can be included on the distal end of a catheter, so that the catheter is usable as a "guidewire with eyes." Thus, the following discussion, which repeatedly uses the term "scanning fiber endoscope" is intended to generally represent one type of catheter with imaging capability, but should not be viewed to limit the technology to that type of scanning device.

The smaller overall circular diameter of an endoscope is ideal for reaching previously inaccessible regions of the human body such as the more peripheral airways, to enable sight-directed cytological sampling in these small lumens. Current practice that relies on a larger sized bronchoscope with separate biopsy or working channels for cell sampling often blindly use the cell sampling tool after it has been extended beyond the view from the standard bronchoscope, and deep into the peripheral airways. This blind cell sampling (or sampling that relies on CT, fluoroscopy, or MRI imaging to guide the biopsy) either produces very low diagnostic yields or adds cost and complexity to the procedure, when used for diagnosing suspected disease in the lungs. This problem also applies to many other regions of the human body, such as the urinary tracts, pancreatic and biliary ducts, sinus cavities, ear canal, etc.

The following discusses several different cannula tools and means for employing these tools to take cell or tissue samples for diagnosis while imaging the tissue. The mechanisms for applying the cannula tool can be one or a combination of:

1. pushing the cannula tool over a more stationary scanning fiber endoscope;
2. retracting a scanning fiber endoscope while holding the cannula tool stationary;

3. using a helical thread for advancing/retracting the cannula tool with respect to the scanning fiber endoscope;

4. releasing a spring-loaded, previously retracted cannula tool over a scanning fiber endoscope, so that the cannula tool is propelled, for example, with a helical spring;

5. employing a pneumatic or fluid push mechanism, such as a balloon, for applying pressure to stabilize an endoscope during use of a cannula tool;

6. applying a vacuum to fluid that draws the cannula tool forward relative to the scanning fiber endoscope;

7. applying a vacuum to the tissue that brings the tissue closer to the cannula tool/endoscope;

8. applying an active force electrically proximate to the distal end of the scanning fiber endoscope/cannula tool to release a trigger or apply a force that causes the cannula tool to interact with adjacent tissue;

9. applying an active force with a piezoelectric actuator coupled with a mechanical lever mechanism to increase a displacement of the cannula tool; or 10. applying an active force with a prime mover, such as a rotational electric motor, linear electric motor, etc.

A portion of the cannula tool, for example, a balloon that can be inflated, can be used as an anchor to stabilize the cannula tool and scanning fiber endoscope relative to adjacent tissue. Especially for high-resolution imaging, slow-frame-rate imaging, or where the tissue is moving due to blood flow, muscle contraction, breathing, etc., it can be important to stabilize the tissue with respect to the endoscope and cannula tool. If a cannula tool needle or forceps is being used to take a biopsy, the needle or forceps can be inserted into or onto the tissue to help stabilize the endoscope for imaging, diagnosis, and/or administration of therapy. The same needle or forceps can also be used to take cell or tissue samples for cytological or pathological analysis. As another example of a stabilizing feature on a cannula tool, one or more balloons like those sometimes used with a catheter can be inflated to stabilize the endoscope and the cannula tool inside a lumen of a patient's body, so that when the tissue of the lumen moves, the endoscope and cannula tool move together so no relative motion is apparent. In addition, the endoscope and/or cannula tool can be provided with barbs that engage adjacent tissue, to hold the cannula tool in place. Alternatively, when a tissue sample that has been cut away at a site is removed for biopsy, the barbs can hold the released biopsy sample as the cannula tool is withdrawn.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1A (Prior Art) is a schematic end view of a conventional multi-channel bronchoscope, showing the multiple channels used for carrying out different functions;

FIG. 1B is a cross-sectional schematic view of a flexible endoscope inside a cannula tube, in accord with the present approach;

FIG. 2A is a simple schematic diagram of a flexible endoscope being used as a guidewire-with-eyes for a cannula tube, defining an annular passage between the two components;

FIG. 2B is a simple schematic diagram of a cannula tool with a bristle brush that is guided by a flexible endoscope;

FIG. 2C is a simple schematic diagram of a cannula tool comprising a biopsy needle that is guided by a flexible endoscope;

FIG. 3 is a schematic diagram illustrating portions of an exemplary scanning fiber endoscope used for guiding a cannula tool to a desired site;

FIG. 9 is a schematic view of an exemplary embodiment of a cannula tool having an inflatable balloon with an abrasive surface, within a body lumen, illustrating the inflatable balloon in a deflated state;

FIG. 10 is a schematic view of the exemplary embodiment of FIG. 9 after the balloon has been selectively inflated and either rotated or moved longitudinally so that the abrasive surface frees cells from tissue on the inner surface of the body lumen, enabling the cells to be drawn into an annular passage between a guidewire and inner surface of the cannula lumen;

FIGS. 17 and 18 are schematic views of an exemplary cannula tool that includes a compressed helical spring for thrusting a bevel needle end into adjacent tissue, in which the compressed spring is selectively released, wherein FIG. 17 shows the cannula tool before the helical spring is released, and FIG. 18 shows it after the helical spring is released;

Figure 19:
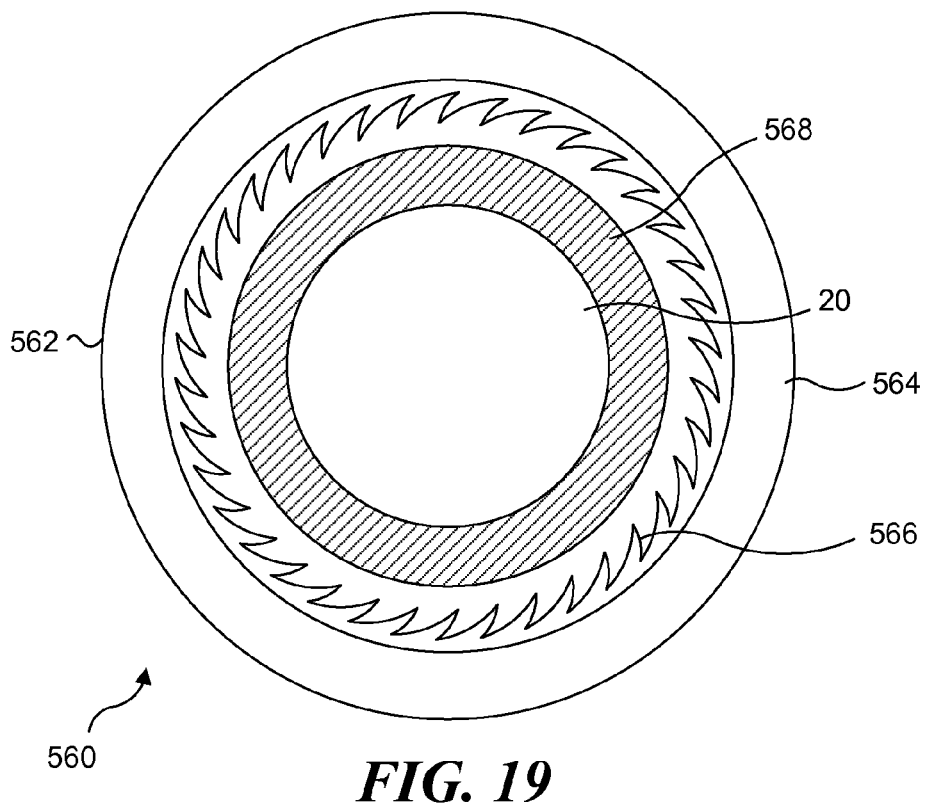
Figure 20:
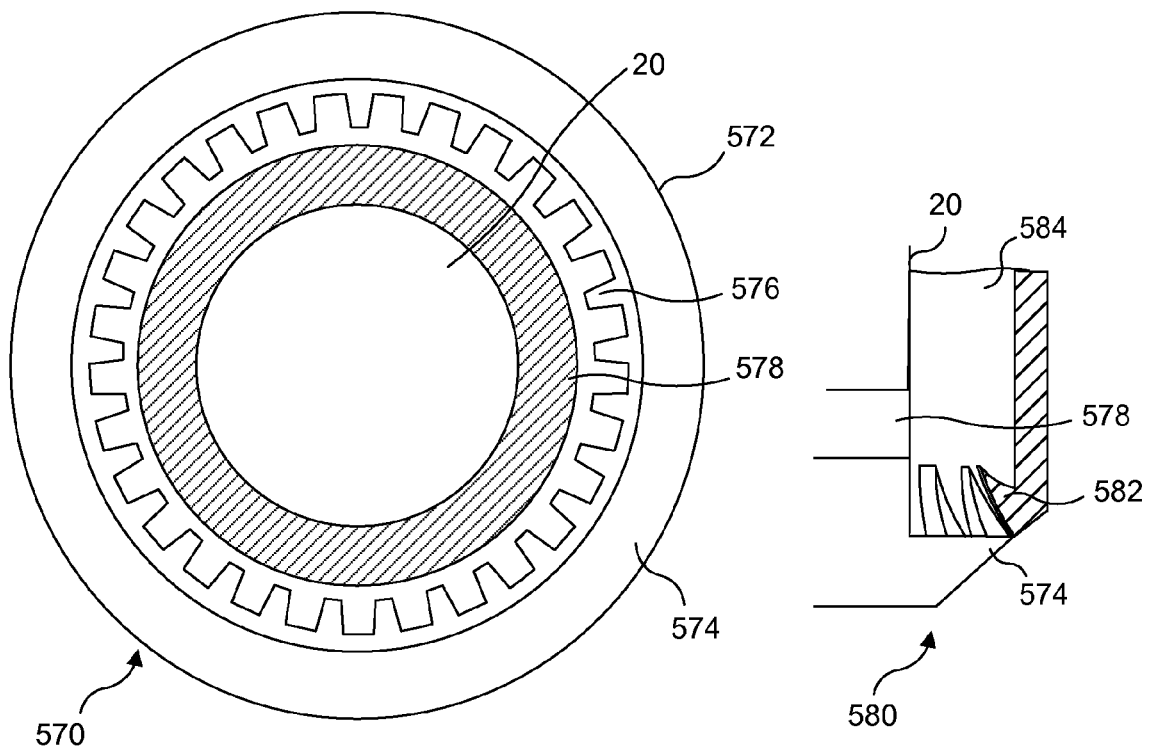
Figure 21:
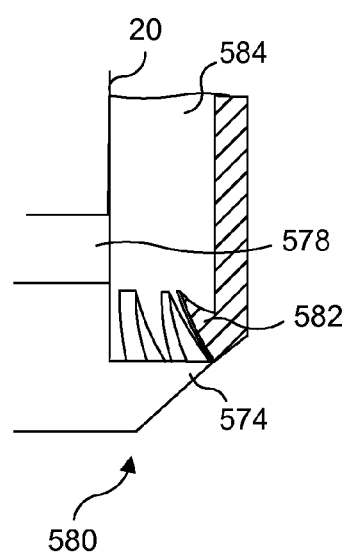
Figure 23:
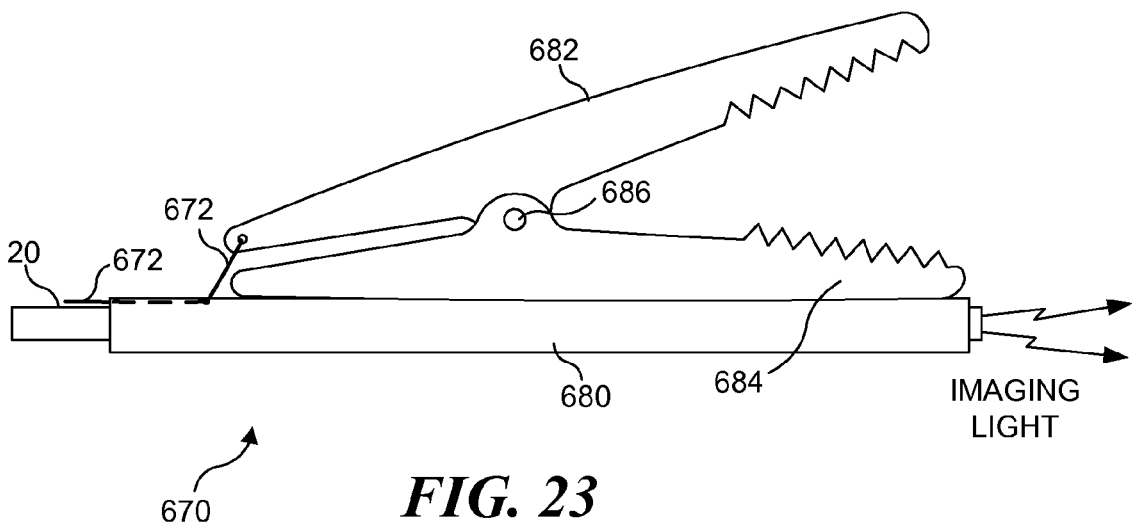
Figure 25:
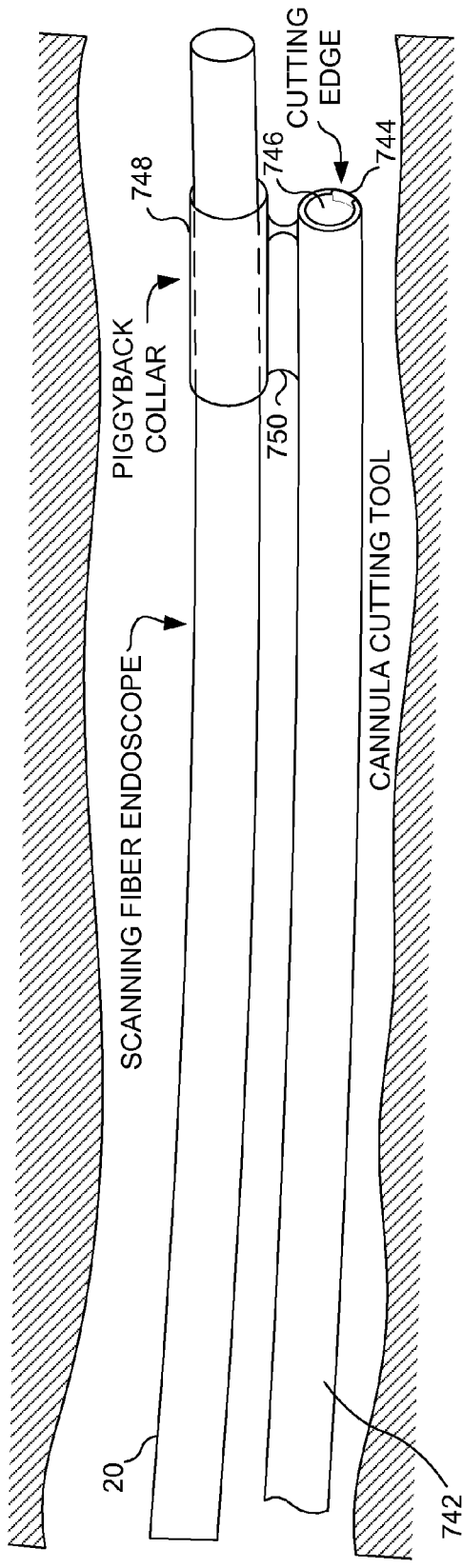
Figure 26:
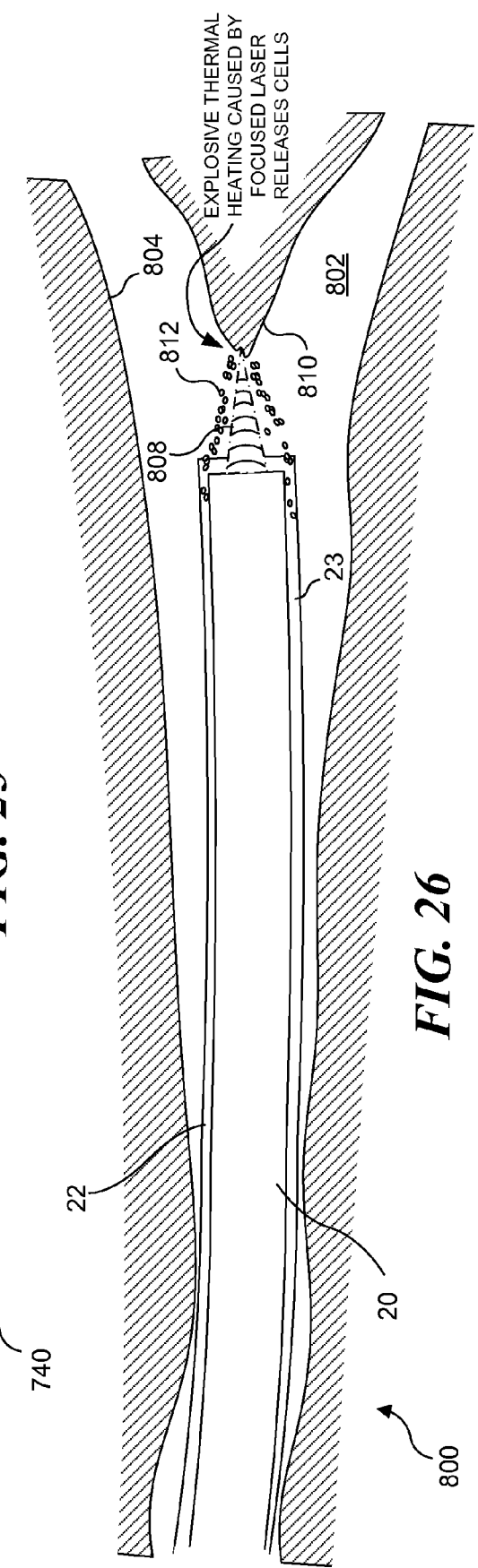

FIGS. 19, 20, and 21 show three different exemplary embodiments of bevel needle ends that respectively include barbs, backward angled teeth, and helically angled barbs, for holding the cannula tool engaged with tissue, and for retaining cells and tissue as a biopsy sample;

FIGS. 22A, 22B, 22C, 22D and 22E respectively illustrate a side view, a distal end view, a side view with jaw open, a side view with jaws open and the guidewire with eyes retracted, and a side view with jaws grasping tissue, for a first exemplary embodiment of forceps that are used with a guidewire with eyes;

FIG. 23 is a side view of another exemplary embodiment of forceps adapted to slide over a guidewire with eyes and are used to grasp tissue;

FIGS. 24A, 24B, 24C, 24D, and 24E respectively illustrate a side view, a side view with jaws open, a distal end view, a phantom side view showing a cannula shaft used to force the jaws to open, and an alternative embodiment where the cannula shaft is used in a different manner to force the jaws open, for forceps mounted on a guidewire with eyes, for use in grasping tissue;

FIG. 25 is a schematic view of an exemplary embodiment of a cannula tool that includes a piggyback guide collar that is adapted to slide over a scanning fiber endoscope, and which has a cutting edge on a leading distal end of a lumen, so that a piece of tissue cut from tissue can be drawn into the lumen for collection at the proximal end of the cannula tool; and FIG. 26 is a schematic diagram of an exemplary cannula tool that includes an annular passage for conveying cells that are released from tissue by explosive thermal heating caused by a focused laser pulse.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

FIG. 1A (Prior Art) shows an end-view of the distal tip of a typical conventional multi-channel bronchoscope 10 with the capability of being selectively bent and having four channels within a 6.2 mm outer diameter. The approach used in this embodiment employs two illumination channels 12 and one camera channel 14. For image-guided interventions like cell/tissue sampling, a working channel 16 having a 2.8 mm diameter is used, as in this example (which uses a PENTAX, type EB-1970K bronchoscope), while smaller working channels of 2.0 mm diameter can be used in smaller 5.2 mm OD bronchoscopes (e.g., those available from Olympus). Surrounding the four channels is an articulated tube 18 that is manipulated by side wires (not shown), which extend proximally outside a patient's body and are pulled to bend the tip of the tube. Care must be taken not to bend the structure too sharply, since doing so might damage the optical fiber bundles in illumination channels 12 that are used for illumination, to enable imaging with a camera through cameral channel 14.

Simply by combining all three imaging channels into one, a scanning fiber endoscope, which is used as an exemplary embodiment of a "guidewire with eyes" saves about ⅔ of the diameter of a conventional bronchoscope. Details of an exemplary scanning mechanism used in the flexible scanning endoscope are discussed below in connection with FIG. 4. As noted above, other imaging devices can be used with a catheter that also serves as a guidewire for cannula tools, within the scope of the approach described below, and it is not intended that the following description, which focuses on the use of a scanning fiber endoscope for such a device should in any way limit the scope of the present approach.

An exemplary scanning fiber endoscope 20 within a cannula tube 22 is shown in FIG. 1B. As will be evident from the Figure, the flexible scanning fiber endoscope of this embodiment is only 0.95 mm in diameter and readily fits within the 1.5 mm outer diameter of cannula tube 22. The cannula tube is thus sized and shaped to readily slide over an elongate flexible shaft of the scanning fiber endoscope. The relatively small size of this configuration enables it to be advanced into much smaller body lumens, such as the smaller passages within a patient's lungs, than conventional bronchoscopes, such as bronchoscope 10. Also, by using the scanning fiber endoscope as a guidewire for cannula tube 22, various types of cannula tools can be employed adjacent to the distal end of the scanning fiber endoscope. In many cases, such tools will be used to free cells or tissue from the internal site and then to facilitate collection of the cells or tissues, which comprise a biopsy sample.

FIG. 2A shows a simple cannula tube over the sub-millimeter guidewire-with-eyes for taking cells from an internal site through an annular gap 23 defined between the outer surface of the endoscope and the inner surface of the cannula tube, for example, using lavage to wash the cells free and then extract them through the annular gap. Annular gap 23 is formed because cannula tube 22 is sized sufficiently larger in diameter than the flexible shaft of the scanning fiber endoscope to provide such a generally annular passage. This exemplary embodiment can also be used for applying a vacuum to adjacent tissue that draws the tissue closer to the distal end of the cannula tool or draws the cannula tool closer to the tissue. FIG. 2B shows a tubular-style cytology brush 24, which can be made from clear plastic and is useful for image-guided cell sampling by abrasion when extended beyond the guidewire-with-eyes and moved over tissue, e.g., the tissue on the inner surface of a lumen. FIG. 2C shows a sharpened tip 26 (i.e. a beveled end) on the distal end of cannula tube 22, which comprises a biopsy needle. The sharpened distal tip slides over endoscope 20, i.e., over the guidewire-with-eyes, and can be image-guided to a desired spot on tissue within a patient's body. The biopsy needle can be thrust into adjacent tissue, to stabilize the guidewire-with-eyes, while imaging or to ensure that the imaging is not adversely affected by movement of the tissue due to cardiovascular motion, or respiratory motion. Those knowledgeable of this art will appreciate that the use of image-guided cannula tools such as these for cell sampling has not previously been accomplished in the bronchoscopy field. Further details and other types of cannula tools that are useable in connection with an endoscope that also serves as the guidewire for the cannula tools are discussed below.

Further Details of Exemplary Scanning Fiber Endoscope

FIG. 3 illustrates other portions of exemplary scanning fiber endoscope 20. The central technical advance is an optical fiber scanner 28, which is coupled to a flexible shaft 30. The distal end of the scanning fiber endoscope is rigid, housing the micro-fiber scanning mechanism and lenses, as discussed below in connection with FIG. 4. In one exemplary embodiment, the rigid tip length is about 12 mm, while the flexible shaft 30 length can be more than 2 meters long. The flexible shaft holds the fine electrical wires that are coupled to the piezoelectric tube actuator, and a plurality of optical detectors spaced-apart around the distal end of the housing to receive light from internal tissue, producing a signal corresponding to the intensity of the light that is conveyed proximally, for display as an image. Alternatively, a ring of 6 to 12 plastic collection optical fibers (for example, arranged in a 250 micron thick ring) can be deployed around the scanning mechanism to receive light from tissue within a patient's body that is illuminated with light from the scanning mechanism. Both the quartz singlemode optical fiber and plastic optical fibers are very flexible, and their sharp bend angles with a bend radius of up to about 5 mm cause no detrimental physical or optical effects.

Scanning fiber endoscope images are generated one pixel at a time as a scanned spot of RGB illumination illuminates the internal tissue with light having an intensity of less than 6 mW. The backscattered light is collected in a non-confocal geometry by the optical detectors (or by the plastic collection optical fibers surrounding the 1 mm optical fiber scanning system, with final detection at the base station). As a further alternative, by using a singlemode optical fiber with dual cladding as the optical fiber scanner, high-efficiency collection of the backscattered light within the inner cladding can be achieved. As a further alternative, a side-viewing optical fiber scanning endoscope can be employed that illuminates tissue at the side(s) (and optionally forward) of the endoscope and collects light scattered from the tissue for imaging. The scanning fiber endoscope is portable and has been used for in vivo imaging of pig airways as a daughter scope through a working channel of a flexible bronchoscope.

Exemplary Scanning Mechanism

Figure 4:
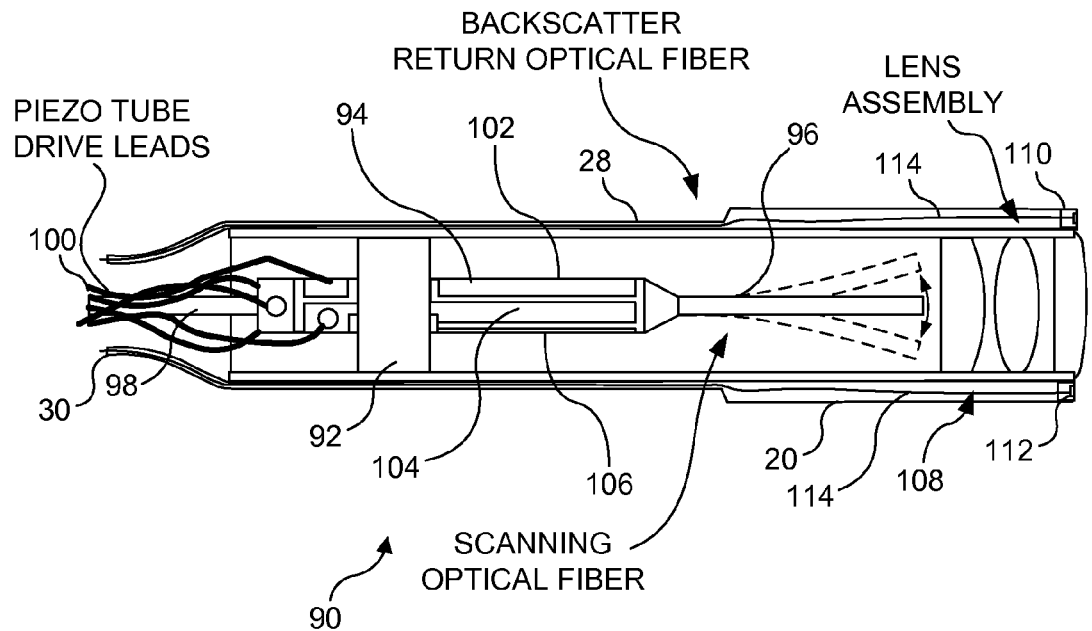
FIG. 4 is a cut-away schematic view of an exemplary scanning mechanism usable in the scanning fiber endoscope that is employed to guide cannula tools to a desired site.

FIG. 4 shows an exemplary scanning mechanism 90 for use in the scanning fiber endoscope described above. Scanning mechanism 90 comprises flexible single mode optical fiber 98 that is supported by a tube 94 of piezoelectric material, which serves to drive a distal end 96 of the optical fiber to move in a desired scanning pattern. Distal end 96 extends distally beyond the tube of piezoelectric material and is cantilevered from it, generally within the center of the flexible scanning fiber endoscope and adjacent to its distal end. This tube of piezoelectric material is held in the endoscope by a base 92. Quadrant electrodes 102, 104, and 106 (and one other that is not visible in this view) are plated onto the tube of piezoelectric material and can be selectively energized with an applied voltage in order to generate two axes of motion in distal end 96 of optical fiber 98. Lead wires 100 carry electrical voltage signals to each of the quadrant electrodes to energize the piezoelectric material relative to each axis of motion. In this exemplary embodiment, the two axes are generally orthogonal to each other. An amplified sine wave applied to one axis and a cosine wave applied to the other axis of the tube piezoelectric material generate a circular scan, although those of ordinary skill in the art will understand that a variety of different scan patterns can be produced by appropriately moving distal end 96 of optical fiber 98. An appropriate modulation of the amplitudes of the electrical voltage signals applied to the quadrant electrodes can create a desired area-filling two dimensional pattern for imaging with light emitted from distal end 96 of the optical fiber. A few examples of the various scan patterns that can be achieved include a linear scan, a raster scan, a sinusoidal scan, a toroidal scan, a spiral scan, and a propeller scan. In some exemplary embodiments, the distal end is driven so that it moves at about a resonant (or near-resonant) frequency of the cantilevered distal end of optical fiber 98, which enables a greater scan amplitude to be achieved for the given drive signals applied. FIG. 4 shows the first mode of lateral vibratory resonance of the cantilevered distal end of the optical fiber.

Other types of scanning mechanisms can alternatively be used for the guidewire with eyes approach. For example, a micro-mechanical electrical systems (MEMS) scanner (not shown) that has a scanning beam used to optically scan an internal site with light to produce an image of the internal site might instead be used. An example of a MEMS scanner for imaging is shown in commonly assigned U.S. Pat. No. 6,975, 898, the disclosure and specification of which are specifically hereby incorporated herein by reference.

Light emitted from distal end 96 as it moves in the desired scan pattern travels through a lens assembly 108 and is directed at the tissue forward of the scanning fiber endoscope. Light reflected or scattered by the tissue illuminated with the scanning light is then detected. In this exemplary embodiment, an annular ring 110 on which a plurality of spaced-apart optical detectors 112 are mounted is disposed around the distal end of the scanning fiber endoscope. Optical detectors 112, which may comprise photodiodes or other light sensitive devices, produce output signals indicative of the intensity of the light that they receive from the internal tissue, and these output signals are conveyed proximally through flexible shaft 30 of the scanning fiber endoscope over conductive leads 114. The output signals conveyed by these conductive leads are then used to produce an image of the internal tissue proximate to the distal end of the scanning fiber endoscope, for example on a monitor. As noted above, a side-viewing scanning fiber endoscope having a reflective surface (not shown) can optionally be used to image tissue at one or more sides of the scanning fiber endoscope.

Exemplary Cannula Tools

Figure 5A:
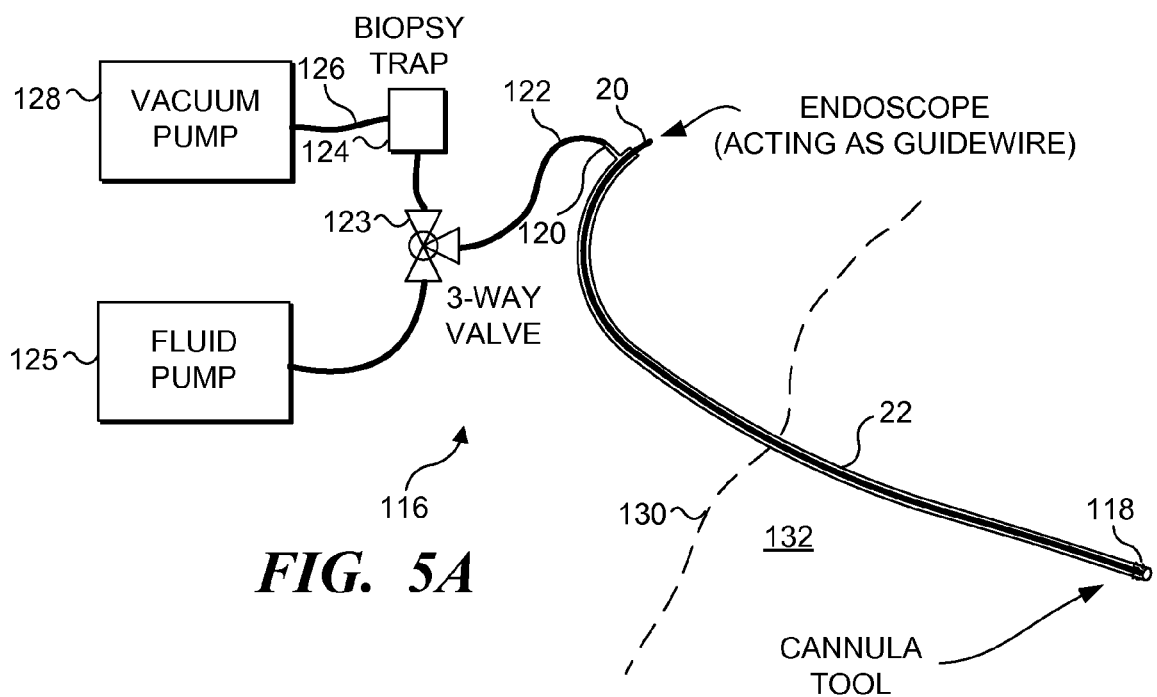
FIG. 5A is a schematic block diagram of an exemplary multifunctional cannula tool and scanning fiber endoscope for collecting a biopsy sample from an internal site in a body of a patient.

FIG. 5A illustrates an exemplary cannula tool system 116 that includes an exemplary cannula tool 118. In this schematic illustration, flexible cannula tube 22 is illustrated extending through a dermal interface 130 and into a body 132 of a patient. Elongate flexible cannula tube 22 is guided to a desired location within body 132 by scanning fiber endoscope 20, which has been inserted through an incision or other opening in dermal interface 130 and has already been advanced to the desired location or site. Flexible cannula tube 22 is then slid over scanning fiber endoscope 20 and is thus guided to the desired location within the patient's body.

After thus being advanced to the desired location, cannula tool 118 can be employed to carry out a plurality of functions. Specifically, cannula tool 118 is employed to dislodge cells or tissue at the desired location, and then facilitates withdrawal of the dislodged cells or tissue from the site as a biopsy sample, for collection to enable further processing or analysis. The dislodged cells or tissue are conveyed from the site at the distal end of the cannula tube through annulus 23 toward the proximal end of the cannula tube. As noted above, annulus 23 is formed between the outer surface of scanning fiber endoscope 20 and the interior surface of cannula tube 22. In this exemplary embodiment, a port 120 is formed at or adjacent to the proximal end of cannula tube 22, in fluid communication with the annulus, and is coupled to one end of a fluid line 122. The other end of fluid line 122 is connected to a three-way valve 123, which selectively provides direct communication to a vacuum pump 128 for applying negative pressures or to a fluid pump 125 for applying positive pressures. Optionally, a biopsy trap 124 is disposed between the three-way valve and vacuum pump (or other source of a vacuum). Vacuum pump 128, which is coupled through a fluid line 126 to the opposite side of biopsy trap 124 produces a negative pressure that draws the biopsy sample, e.g., along with a bodily fluid such as blood, mucus, or an introduced fluid (e.g., air or saline), into the biopsy trap. The biopsy sample can then be removed from the biopsy trap so that the processing and analysis can be carried out. Fluid pump 125 can provide saline solution (from a source reservoir—not shown) to suspend the dislodged cells or tissue for easier retrieval. Furthermore, the introduced fluid under positive pressure can help to dislodge cells, mucus, blood, or other bodily fluid from the tool, scanning fiber endoscope, or wall of the body lumen. It should also be noted that vacuum pump 128 can be employed to draw tissue closer to the distal end of a cannula tool or alternatively to draw the distal end of the cannula tool closer to the tissue, using the force exerted by ambient pressure that is greater than the reduced pressure created by the vacuum pump.

Figure 5B:
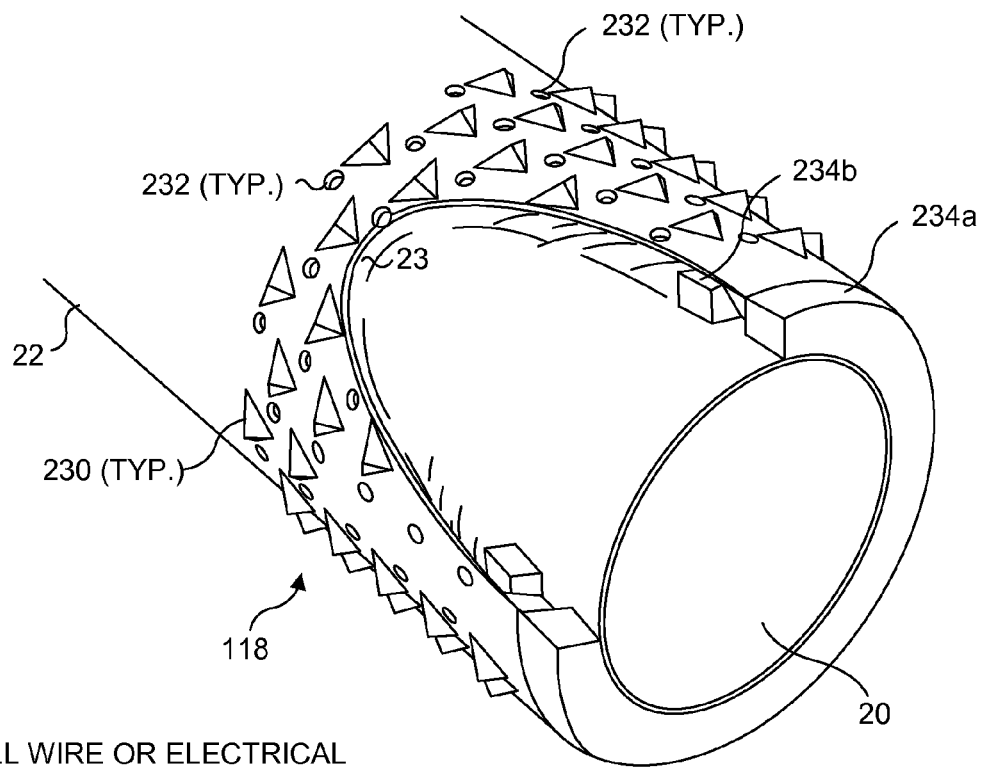
FIG. 5B is an enlarged cut-away schematic view of an exemplary embodiment of a distal end of a cannula tool that includes an abrasive surface for abrading cells from adjacent tissue.

Further details of cannula tool 118 are illustrated in FIG. 5B. Cannula tool 118, which is shown being guided by scanning fiber endoscope 20, includes a plurality of spaced-apart outwardly extending points 230 disposed around the exterior surface of cannula tube 22. Points 230 are shaped so that they tend to abrade cells from tissue adjacent to the outer surface on which the points are disposed when the cannula tube is moved longitudinally back-and-forth a few centimeters (and/or rotated back and forth around) its longitudinal axis. A plurality of orifices 232 are interspersed between the plurality of points providing a number of fluid communication paths through which the bodily fluid and cells dislodged from the adjacent tissue can be drawn into an annulus 23, which is disposed between the outer surface of scanning fiber endoscope 20 and the inner surface of cannula tube 22. As explained above in connection with FIG. 5A, the bodily fluid conveys the dislodged cells or tissue through annulus 23 from the distal end of the elongate flexible tube to the proximal end where port 120 is disposed, so that the cells or tissue comprising the biopsy sample can be drawn into biopsy trap 124 and collected for processing.

A seal comprising annular rings 234*a* and 234*b* is disposed at the distal end of cannula tube 22 to ensure that vacuum pump 128 draws the bodily fluid and dislodged cells or tissue through orifices 232, rather than simply drawing bodily fluid without the cells or tissue from around scanning fiber endoscope 20 at the distal end of the cannula tube. It will be understood that the shape or configuration of points 230 are intended to be exemplary and not in any way limiting, since it should be apparent that a number of other different shapes or configurations can be employed for such points comprising an abrasive surface, such as short bristles (e.g., a tubular brush). Further, either more or fewer points 230 can be disposed on cannula tool 118, over either a longer or shorter length section of cannula tube 22.

Figure 5C:
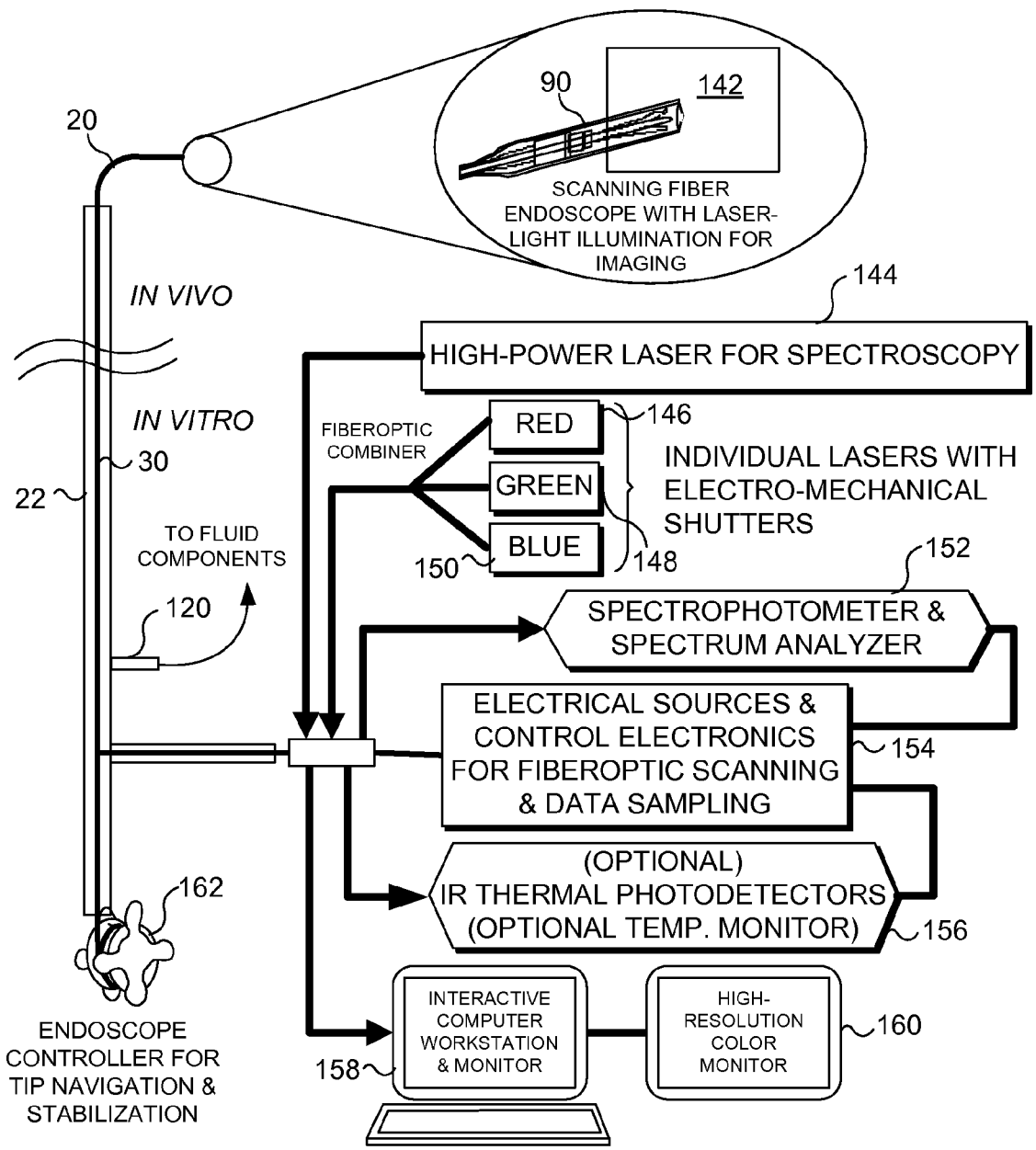
FIG. 5C is a schematic block diagram of an exemplary system used by the scanning fiber endoscope for imaging, performing diagnostic evaluation, and rendering therapy to a site within a patient's body.

FIG. 5C is a schematic block diagram of an exemplary system 140 for use by the scanning fiber endoscope for imaging an internal site 142 using the signals produced by scanning mechanism 90 (details of which are shown in FIG. 4). To simplify this Figure, details of the components involved in providing fluid, vacuum, and collecting the biopsy sample that are discussed above in connection with FIG. 5A are not replicated in this view. A high-power laser 144 that can be used for spectroscopy analysis of internal site 142 is optionally included in system 140. Also provided as light sources are red, green, and blue (RGB) lasers 146, 148, and 150, respectively. These lasers are selectively controlled with electromechanical shutters (not shown) and their output laser light beams are combined with a fiber optic combiner for transmission down the optical fiber to the scanning mechanism. In connection with the optional high-power laser for spectroscopy, a spectrophotometer and spectrum analyzer 152 is also optionally included in system 140. This system includes a block 154, which comprises several electrical sources and control electronics for fiber optic scanning and data sampling, which are used for imaging internal site 142 with scanning mechanism 90. Optionally, one or more infrared (IR) thermal photodetectors and a temperature monitor 156 can be included, to track the temperature of the internal site, which can be important if therapy is being rendered, or for diagnostic purposes. An interactive computer workstation and monitor 158 and a high-resolution color monitor 160 are also included to enable an operator to view images of internal site 142 and to facilitate advancing the scanning fiber endoscope to a desired location in a patient's body. The imaging capability can be particularly important if advancing the scanning fiber endoscope through a labyrinth of linked passages, e.g., the bronchial passages in a patient's respiratory system. The images of anatomical features and tissue enable the medical practitioner to readily select a path along which to manipulate and control the direction along a path being followed by the distal end of the endoscope to reach a desired location in a patient's body. An endoscope controller for tip navigation and stabilization 162 is schematically illustrated and is intended to indicate that means are provided for controlling the endoscope as it is navigated through one or more lumens or along a path in a patient's body.

Figure 6:
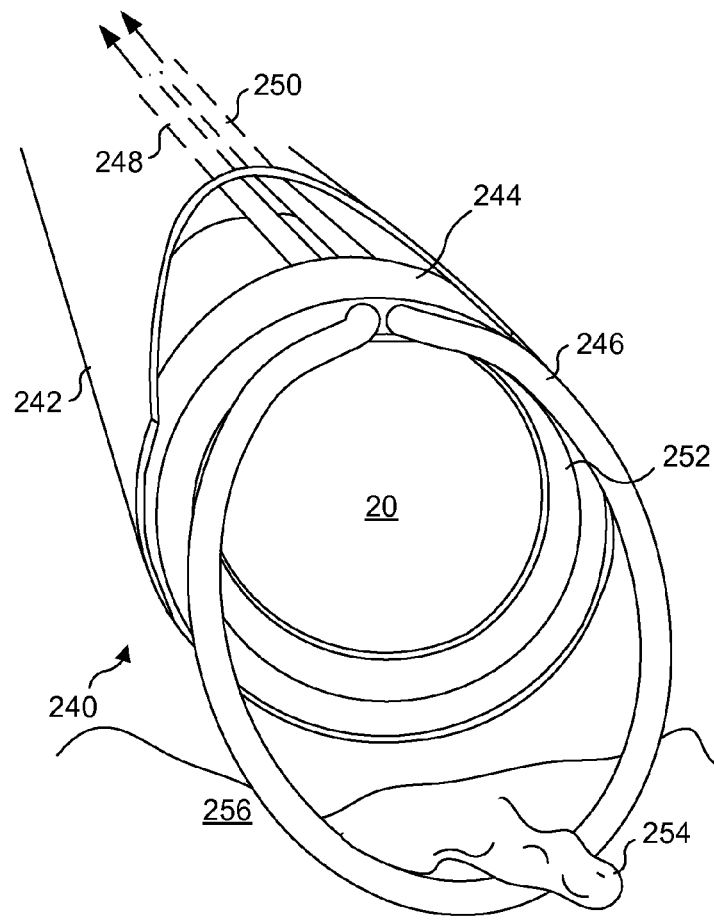
FIG. 6 is an enlarged cut-away schematic view of a distal end of an exemplary embodiment of a cannula tool that includes a loop for snaring tissue that is cut away for a biopsy sample.

In FIG. 6, an exemplary cannula tool 240 is illustrated for use in connection with an elongate flexible tube 242. This same outer tube can also be used to shield the internal tissues of the body from cannula tool 118 during insertion to the desired location within the body. This outer elongate flexible tube or sheathing can then be withdrawn to reveal a biopsy tool distal tip when the tip is disposed at the desired biopsy site within the body. As in cannula tool 118, cannula tool 240 is configured to be advanced to a desired site by sliding along scanning fiber endoscope 20. Cannula tool 240 includes a wire loop 246 that extends distally of a ring 244, which is disposed just inside the distal end of elongate flexible tube 242. Loop 246 is sized to ensnare a biopsy sample of tissue, such as a polyp 254 growing from adjoining tissue 256 at the desired site, as shown in this Figure.

Two different techniques can be employed to cut away the piece of tissue comprising the biopsy sample from adjoining tissue. One option is to supply an electrical current so that loop 246 is heated sufficiently to burn through adjacent tissue 256, freeing the biopsy sample, such as polyp 254. The electrical current can be applied to loop 246 through conductive wires 248 and 250, which extend proximally of the elongate flexible tube 242 and are connected through a switch to a conventional electrical current supply (neither shown). Alternatively, one or both of wires 248 and 250 can be pulled proximally of the proximal end of elongate flexible tube 242, which tightens loop 246 around the tissue sufficiently to cut through the tissue, freeing it from the adjacent tissue. To help stabilize the tool over the sample and possibly help to ensnare the tissue, a vacuum can be applied within outer elongate flexible tube 242. Once the biopsy sample is freed, it can be drawn with bodily fluid into an annulus 252 formed between the outer surface of scanning fiber endoscope 20 and the inner surface of the elongate flexible tube 242. For example, vacuum pump 128 (shown in FIG. 5A) can be used to draw the bodily fluid and the dislodged tissue comprising the biopsy sample to the proximal end of the elongate flexible tube 242. This biopsy sample that has thus been freed and withdrawn from inside the body of a patient can then be collected for processing and analysis by medical personnel.

Figure 7:
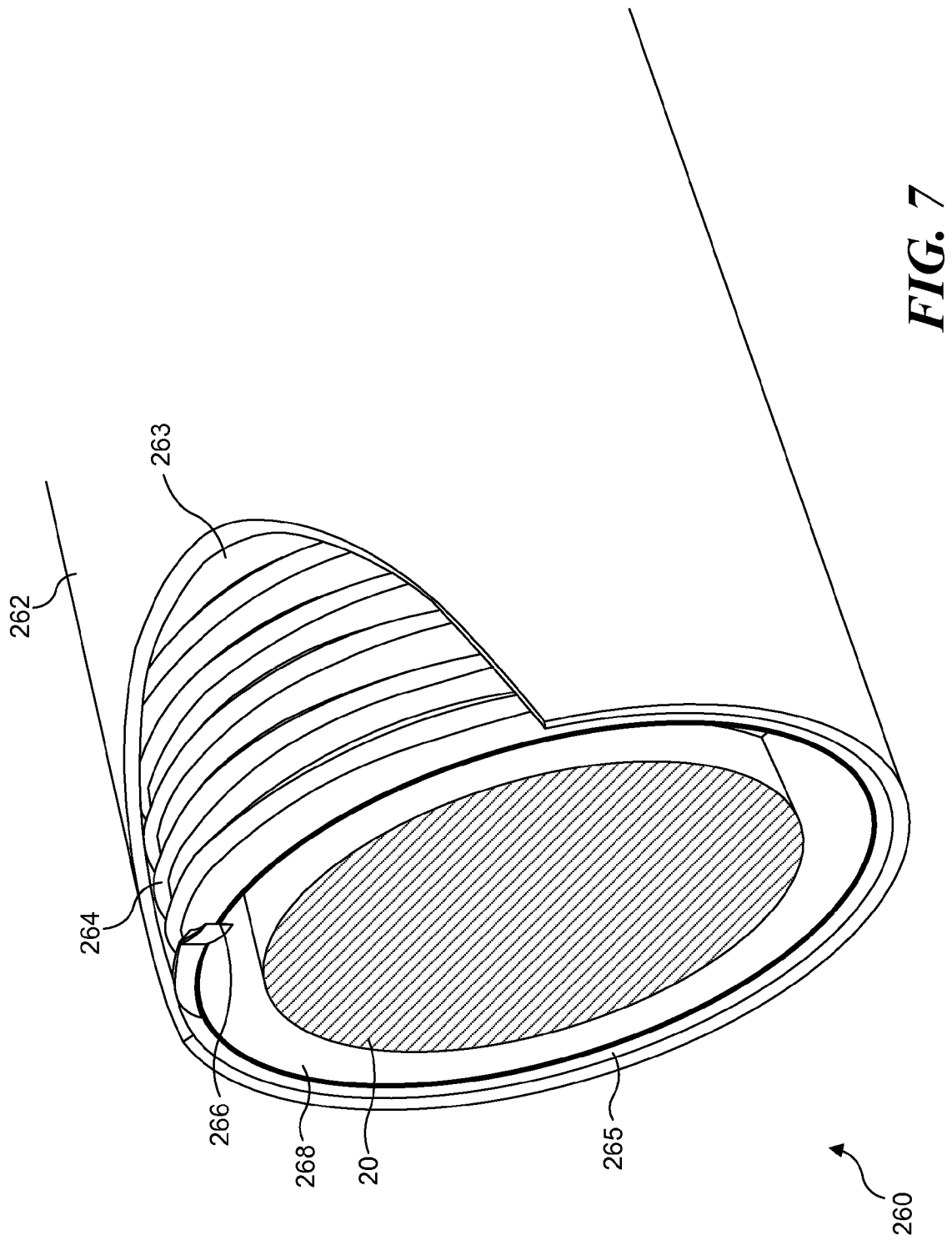
FIG. 7 is an enlarged cut-away schematic view of a distal end of an exemplary embodiment of a cannula tool that includes a helical ribbon having a cutting edge for cutting away a piece of tissue for a biopsy sample.

An exemplary embodiment of a cannula tool 260 shown in FIG. 7 is also configured to be advanced to a desired site within the body of the patient over scanning fiber endoscope 20. Cannula tool 260 includes an outer elongate flexible tube 262 that extends between a distal end and a proximal end. The proximal end is disposed outside the body of the patient. Within the outer elongate flexible tube is disposed a middle flexible tube 265. On the outer surface of the middle flexible tube, at its distal end, is affixed a helical coil 264. The helical coil is in contact with the inner surface of the outer elongate flexible tube and terminates on its leading end at a sharp cutting edge 266, which extends just beyond the distal end of elongate flexible tube 262. Sharp cutting edge 266 is thus configured to slice a ribbon of tissue from the desired site as middle flexible tube 265 is rotated about its longitudinal axis in the appropriate direction with respect to outer elongate flexible tube 262 to bring the sharp cutting edge into the adjacent tissue. This ribbon of tissue, which comprises a biopsy sample, is carried between helical coils 264 and conveyed with bodily or introduced fluid through an annulus 268 formed between the outer surface of scanning fiber endoscope 20 and the inner surface of middle flexible tube 265. A smaller annular gap 263 is provided between the outer surface of middle flexible tube 265 and the inner surface of outer elongate flexible tube 262, which may facilitate capture of the tissue ribbon when negative pressure is applied at the proximal end of the elongate flexible tube or may facilitate removal of the tissue ribbon from the helical coil with introduced fluid applied at the proximal end. As discussed above, the vacuum pump shown in FIG. 5A can be used to draw the biopsy sample and bodily fluid through the annulus toward the proximal end of the elongate flexible tube, where the biopsy sample can be collected.

Figure 8:
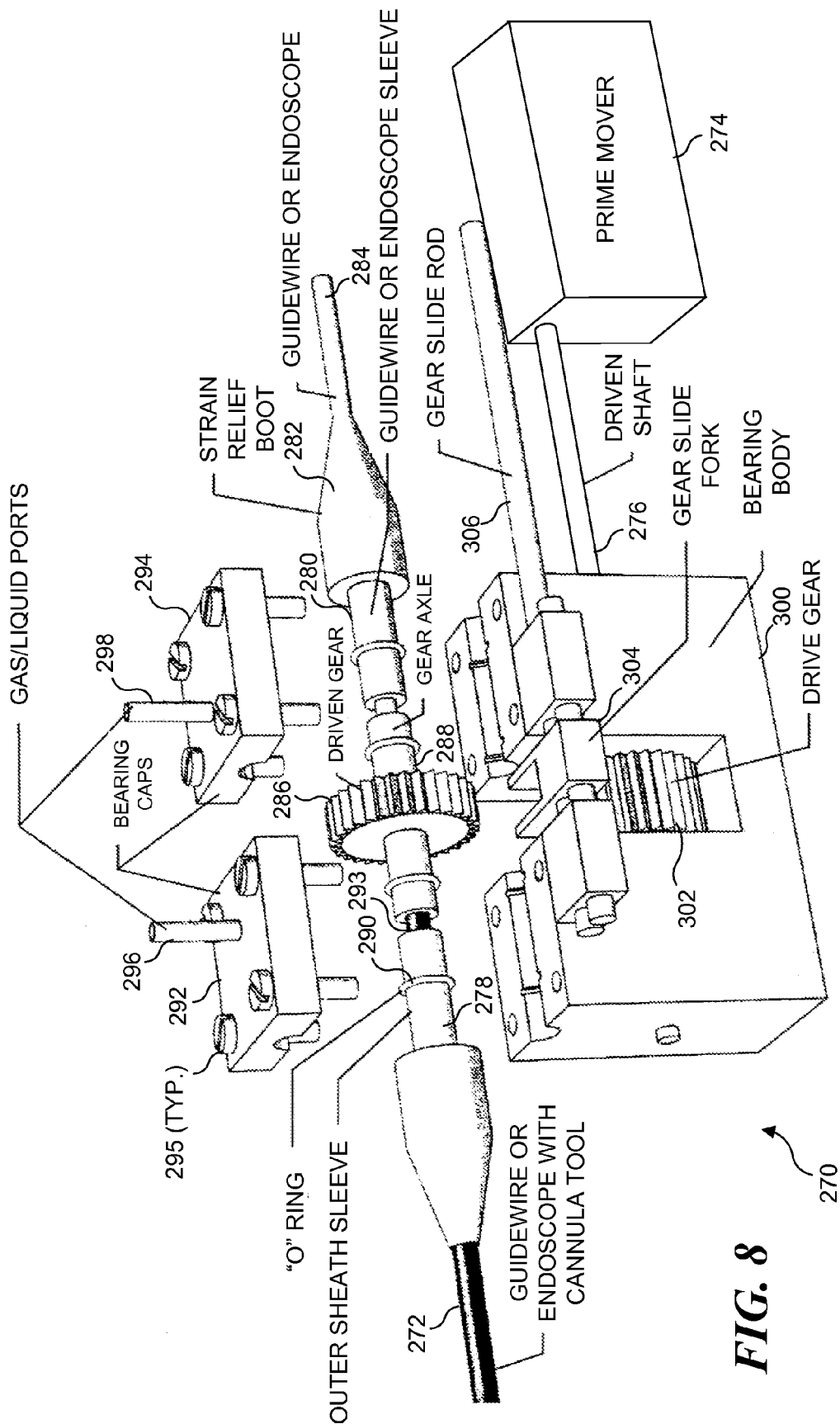
FIG. 8 is an exploded view of an exemplary rotational driver that is disposed externally and is configured to drivingly rotate a cannula tool about a longitudinal axis.

FIG. 8 illustrates a rotational driver 270 that is configured to rotate a cannula tube or scanning fiber endoscope 20 about a longitudinal axis of the scanning fiber endoscope. Attached to the distal end of the cannula tube or scanning fiber endoscope can be one of the multifunctional cannula tools discussed herein. The cannula tube should be viewed as a specific type of "elongate flexible tube," which is used with each of the exemplary embodiments of the cannula tools discussed herein. However, this exemplary embodiment happens to match the ribbon cutting tool in FIG. 7, which optionally can provide fluid communication in both annular gaps around the middle flexible tube.

In connection with rotational driver 270, a prime mover 274 (for example, an electric motor) is included to rotate a driven shaft 276, thereby providing a rotational force that rotates and drives middle flexible tube 265, which holds the biopsy tool, forward and backward. An outer sheath sleeve 278 is fitted over guidewire or endoscope 272. Sealing "O" rings 290 are provided on outer sheath sleeve 278, as well as on each side 288 of a driven gear 286, and on a guidewire or endoscope sleeve 280, which is near a proximal end 284 of the scanning fiber endoscope and attached to a strain relief boot 282. End caps 292 and 294 are fitted over and sealingly engage "O" rings 290, when securely coupled to a bearing body 300 by fasteners 295. End caps 292 and 294 include ports 296 and 298, to provide fluid paths in fluid communication with exposed portions of the scanning fiber endoscope. At each of these exposed portions, the elongate flexible tube is open for withdrawing or injecting either gases or liquids into one or two annular gaps formed for use with cannula tool 272. When combining the components of FIGS. 7 and 8, port 298 can be used to withdraw a biopsy sample that is conveyed with a bodily or introduced fluid from the distal end of the guidewire or endoscope with cannula tool 272, through annulus 268 formed between scanning fiber endoscope 20 and the inner surface of middle flexible tube 265. Port 296 is in fluid communication with small annular gap 263 that is formed between the outer surface of middle flexible tube 265 and the inner surface of outer elongate flexible tube 262. For example, a vacuum can be applied to both ports 296 and 298 in FIG. 8, which will help pull the tissue up against the cutting edge of the cannula tool in FIG. 7. After cutting is completed by advancing helical coil 264 on middle flexible tube 265 toward the tissue by rotating the drive gear that is mechanically coupled with the middle flexible tube, the vacuum can be removed from only the outer annular gap, i.e., from port 296. By applying a saline solution to port 296, any tissue and cells within the helical coil can be flushed and then sucked into the larger inner annulus 268, with negative pressure applied to port 298, e.g., with vacuum pump 125 (FIG. 5A).

Driven shaft 276 is drivingly coupled to a drive gear 302, which is rotatably mounted in bearing block 300 and affixed to an end of driven shaft 276. A gear slide fork 304 is mounted on the side of bearing block 300 and is configured to engage driven gear 286, so as to move the driven gear into meshing relationship with drive gear 302 when gear slide rod 306 is appropriately pushed (or pulled) longitudinally. By thus moving gear slide rod 306, a user can selectively engage driven gear 286 with drive gear 302 to apply a rotational force that begins turning driven gear 286, which is in mechanical communication with middle flexible tube 293, so that the middle flexible tube turns in one direction versus the opposite direction, about its longitudinal axis. Rotational motion of the cannula tool shaft can be used either for abrading or for cutting cells and tissue from adjacent tissue at a desired location in a body of a patient. For example, the rotational driver can be used to rotate a cannula tool having an abrasive surface, such as exemplary cannula tool 118, or can turn a cannula tool that has a sharp cutting edge, which is able to cut away a ribbon of tissue to form a biopsy sample, such as exemplary cannula tool 260.

In FIG. 9, a cannula tool 310 is illustrated and is disposed adjacent to the distal end of a flexible elongate tube 316. As explained above, flexible elongate tube 316 has an internal lumen that is sized to be guided over scanning fiber endoscope 20 to a desired site within a body of a patient. For example, as shown in this Figure, scanning fiber endoscope 20 has been advanced through a body lumen 312 and has been used to guide elongate flexible tube 316 so that a balloon 318 (currently deflated) is advanced to a site where cells comprising a biopsy sample is to be taken. Balloon 318 is sealingly attached to the outer surface of the flexible elongate tube at each end of the balloon (for example, by thermal bonding or using an appropriate adhesive). A pressurized fluid tube 320 extends within an annulus formed between the outer surface of scanning fiber endoscope 20 and the inner surface of elongate flexible tube 316, from the proximal end of the flexible elongate tube to a port 322. Port 322 provides an opening through elongate flexible tube 316 to add or remove fluid volume inside balloon 318. The proximal end of the pressurized fluid tube is coupled to a pressurized fluid source, such as fluid pump 125, and to a negative pressure source, such as vacuum pump 128, both of which are shown in FIG. 5A.

Pressurized fluid provided by the pressurized fluid source can be selectively applied through pressurized fluid tube 320 and port 322 to inflate balloon 318, as shown in FIG. 10. When balloon 318 is thus inflated, an abrasive coating 324 that extends over the outer surface of balloon 318 comes into contact with tissue on the wall of body lumen 312. When the elongate flexible tube 316 is then rotated around its longitudinal axis or pushed/pulled longitudinally back-and-forth within body lumen 312, cells 326 are abraded from the tissue lining the body lumen by the abrasive coating. The abraded cells and bodily fluid within body lumen 312 are together drawn into an annulus 328 formed between the inner surface of the lumen extending through elongate flexible tube 316 and the outer surface of scanning fiber endoscope 20, as shown in FIG. 10. These cells, which comprise a biopsy sample, can be withdrawn from the annulus at the proximal end of flexible elongate tube 316, generally as explained above. An elongate sheath 325 (shown in FIGS. 9 and 10 after the elongate sheath has been pulled back) can be disposed around the abrasive balloon during insertion and retraction and then pulled back proximally to expose the abrasive surface of the balloon when the cannula tool is disposed at a desired site for taking a biopsy sample. The proximal end of elongate sheath 325 is accessible outside the body of a patient and can be separately manipulated to move it longitudinally, relative to balloon 318 (or other embodiments of the cannula tool). For other types of cannula tools, it may be preferable to rotate the elongate sheath about its longitudinal axis between first and second positions, so that an opening at its distal end (not shown) selectively either protects or exposes the portion of the cannula tool that is used to dislodge cells or tissue comprising the biopsy sample.

Figure 11A:
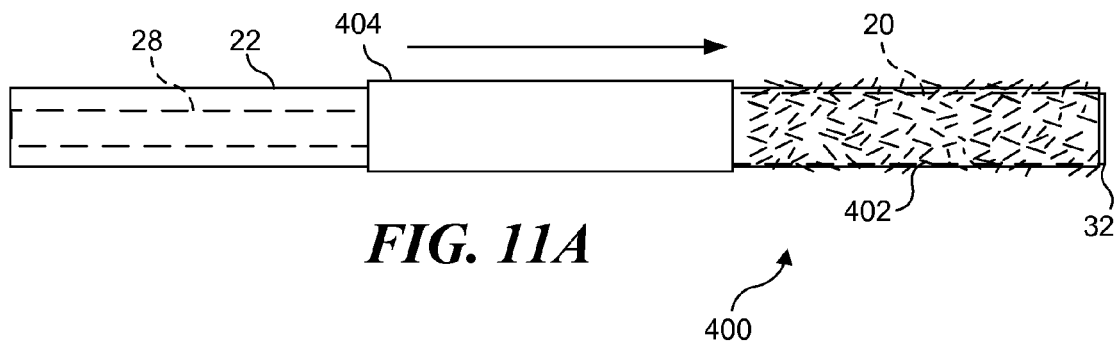
FIGS. 11A and 11B are schematic views illustrating an exemplary embodiment of a cannula tool that includes a bristle brush for collecting a biopsy sample, respectively showing the bristle brush exposed and covered.
Figure 11B:
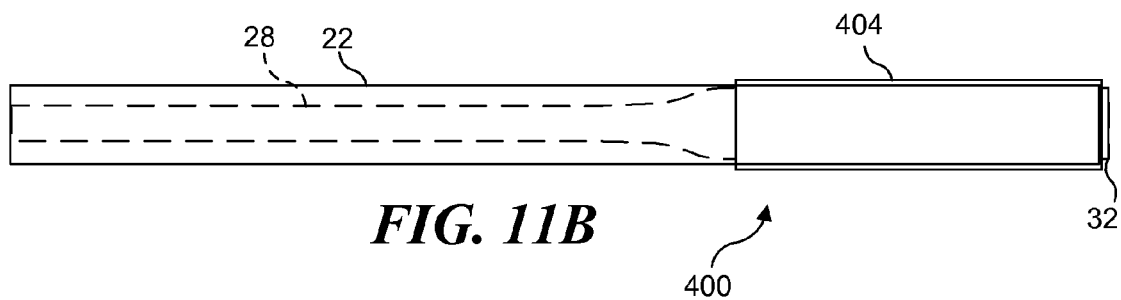

An exemplary cannula tool 400 is illustrated in FIGS. 11A and 11B, which includes bristles 402 disposed over an area of cannula tube 22, proximate the distal end of the cannula tube. These bristles can be used to abrade a biopsy sample comprising cells and tissue, from an interior surface of a body lumen or other adjacent tissue inside a patient's body. When advancing cannula tool 400 into a body over scanning fiber endoscope 20, a protective cover 404 is moved forward over bristles 402, as shown in FIG. 11B, and the protective cover is pulled back using an internal wire or other flexible lead (not shown) that extends through the cannula tube, exposing bristles 402, as shown in FIG. 11A. Alternatively, the protective cover 404 is the distal portion of an outer elongate flexible tube that provides mechanical communication to the proximal end of the cannula tool over guidewire system. Similarly, after a biopsy sample is taken at a desired site, protective cover 404 is drawn forward to again cover bristles 402 and to also cover and protect the biopsy sample that has been collected on the bristles, so that the biopsy sample remains intact as cannula tube 22 and cannula tool 400 are withdrawn from the body of the patient.

Figure 12A:
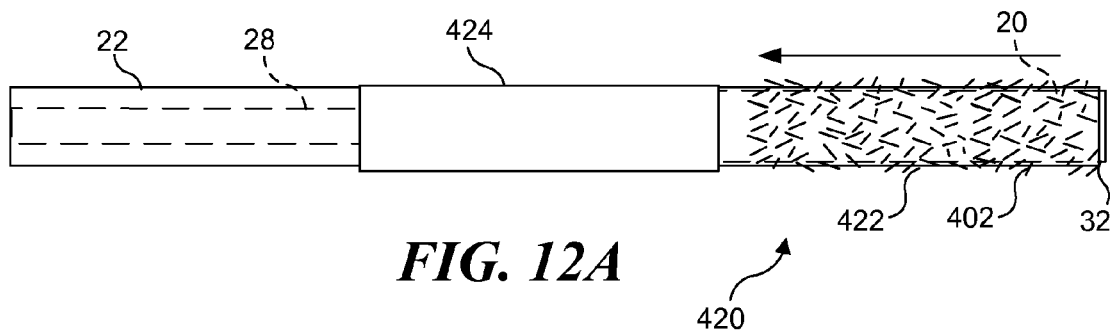
FIGS. 12A and 12B are schematic views illustrating another exemplary embodiment of a cannula tool that includes a bristle brush for collecting a biopsy sample, respectively showing the bristle brush exposed and covered.
Figure 12B:
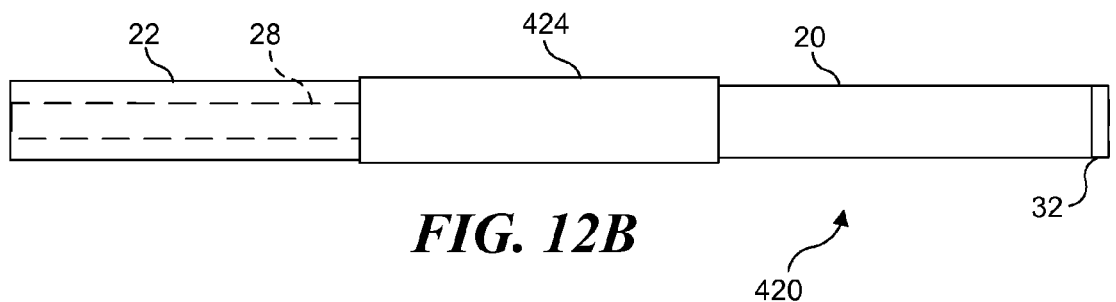

Another related exemplary cannula tool 420 that includes bristles 402 on the distal end of cannula tube 22 is shown in FIGS. 12A and 12B. When inserting cannula tool 420 into a patient's body and while advancing it to a desired site where a biopsy sample is to be taken, cannula tube 22 is positioned so that bristles 402 are covered by a fixed protective cover 424, as shown in FIG. 12B. After the distal end of cannula tube 22 has reached the desired site where the biopsy sample is to be taken, the cannula tube is pushed forward (i.e., distally), while scanning fiber endoscope 20 is held in a fixed position, which exposes bristles 402, as shown in FIG. 12A. Once the bristles have been scrubbed against the adjacent tissue so that cells are scrubbed away and left on the bristles, the cannula tube is drawn backward (i.e., proximally), so that fixed protective cover again covers bristles 402 and the biopsy sample collected there. The cannula tube and scanning endoscope can then be removed from the patient's body together so that the biopsy sample remains covered by the fixed protective cover. Once outside the patient's body, the biopsy sample can be recovered from bristles 402 for further processing and analysis.

Figure 13:
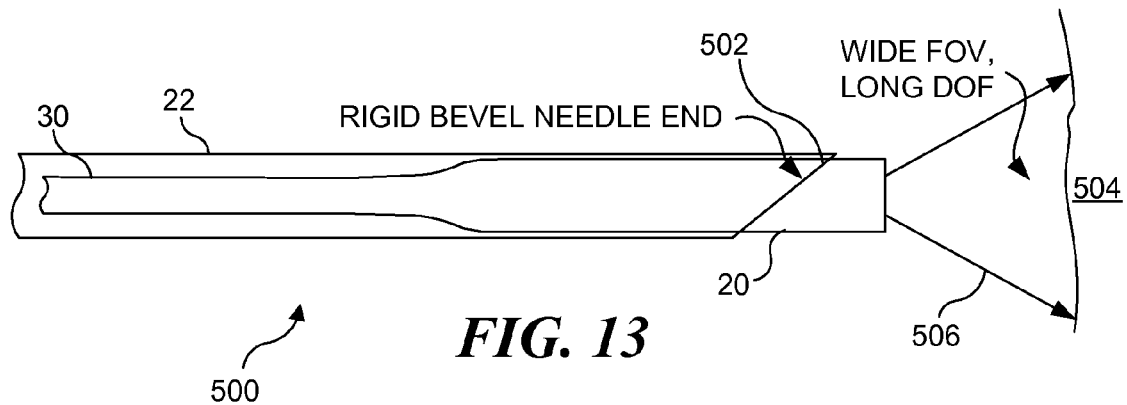
FIG. 13 is a schematic view of an exemplary cannula tool that includes a bevel needle end, illustrating how the scanning fiber endoscope can image a prospective site with a wide field of view and a long depth of field.
Figure 14:
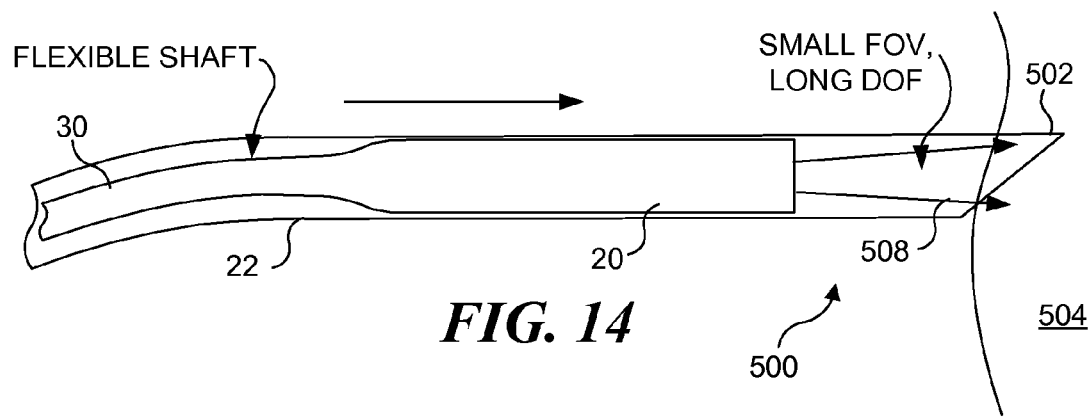
FIG. 14 is a schematic view of the exemplary cannula tool of FIG. 13, illustrating how the scanning fiber endoscope can image the tissue inside the bevel end needle with a small field of view and long depth of field, after the bevel needle end has been plunged into the tissue.
Figure 15:
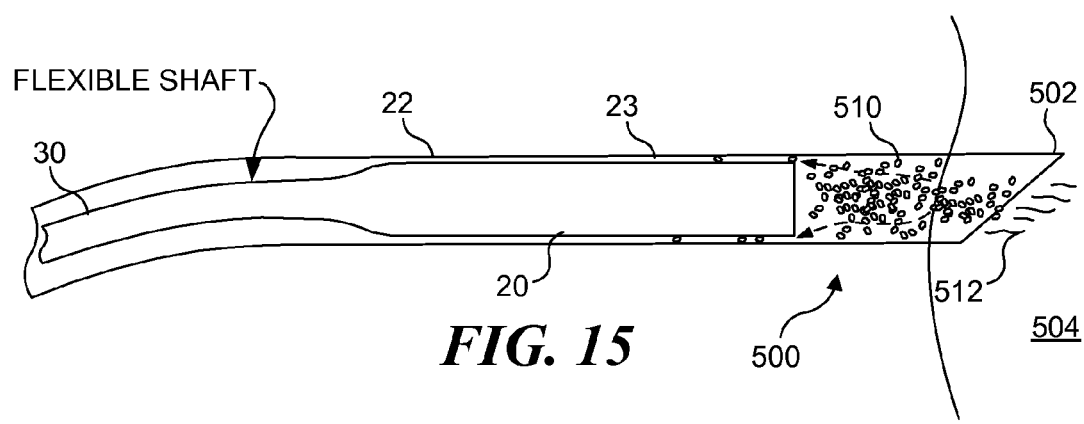
FIG. 15 is a schematic view of the exemplary cannula tool of FIG. 13, illustrating how cells comprising a biopsy sample can be drawn from the tissue within the bevel needle end.

FIGS. 13, 14, and 15 illustrate an exemplary embodiment of a cannula tool 500 that includes a bevel needle end 502, which is rigid and can be forcefully thrust into adjacent tissue 504 to take a biopsy sample comprising cells or tissue that are cut free when bevel needle end 502 is withdrawn from the tissue, or which can be used to cut free a biopsy sample comprising cells that can be flushed from the tissue and carried to the proximal end of cannula tube 22 for collection with a bodily fluid or an introduced fluid, as discussed above. As cannula tool 502 is approaching a potentially desired site 504, scanning fiber endoscope can image the surface of the site using a relatively wide field of view (FOV) and long depth of field (DOF) 506, as illustrated in FIG. 13. If the site appears appropriate to take a biopsy sample, cannula tube 22 is forcibly advanced in the distal direction over scanning fiber endoscope 20, so that bevel needle end 502 pierces the surface of the tissue at site 504, as shown in FIG. 14. A plug of tissue can then be withdrawn with bevel needle end 502 as the cannula tool is pulled proximally, or alternatively, as shown in FIG. 15, site 504 can be washed with a lavage using an introduced a pressurized fluid 512 that is conveyed through cannula tube 22 from fluid pump 125 (FIG. 5A). Pressurized fluid 512 is applied to the tissue through bevel needle end 502, causing cells 510 to be freed from the tissue within the bevel needle end. These cells are then conveyed through the needle and into annular gap 23, drawn by vacuum pump 128 (FIG. 5A), and collected as the biopsy sample.

Figure 16:
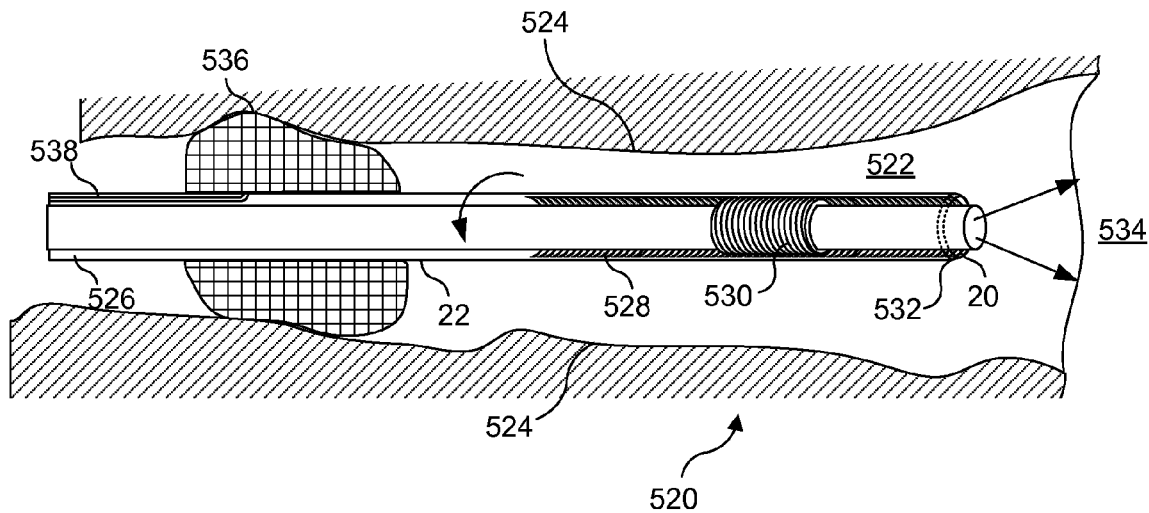
FIG. 16 is a schematic cut-away view of an exemplary cannula tool that includes a helical thread for advancing a bevel needle end into adjacent tissue and a balloon that is inflated for stabilizing the cannula tool/scanning fiber endoscope while imaging the site.

An exemplary embodiment of a cannula tool 520 is illustrated in FIG. 16. In this Figure, cannula tool 520 is shown in a body lumen 522 that is defined by surfaces 524 and is adjacent to a site 534 that is being imaged to determine if it is appropriate to take a biopsy sample. Cannula tool 520 includes a bevel needle end 532 formed on the distal end of cannula tube 22. A helical thread 528 is provided inside the distal portion of cannula tube 22, and the helical thread engages a corresponding helical threaded collar 530 that is affixed on the exterior surface of scanning fiber endoscope 20, a few centimeters from its distal end. As cannula tube 22 is rotated relative to scanning fiber endoscope 20, e.g., by rotational driver 270 (FIG. 8), bevel needle end 532 is advanced forward from the distal end of the scanning fiber endoscope and into the tissue at site 534, enabling a biopsy sample to be taken from the tissue at the site, as generally explained herein. The direction of rotation of cannula tube 22 by rotational driver 270 (or other suitable mechanism—including manual rotation) can be reversed to draw the bevel needle end from the tissue at site 534.

Optionally, a balloon 536 can be inflated inside body lumen 520 to stabilize the scanning fiber endoscope, for example, while imaging site 534. To inflate balloon 536, a pressurized fluid is supplied through a fluid line 538 that extends from a source of pressurized fluid at the proximal end of cannula tube 22 and through a port (too small to be visible in this Figure) in cannula tube 22, which is in fluid communication with the interior of balloon 536. Balloon 356 can be deflated by releasing the pressure within balloon 536 after site 534 has been imaged. By enabling the site to be imaged before a decision is made to take a biopsy sample, scanning fiber endoscope provides clear advantages over conventional approaches that employ touch or external imaging to determine where a biopsy sample should be taken inside a patient's body.

Figure 17:
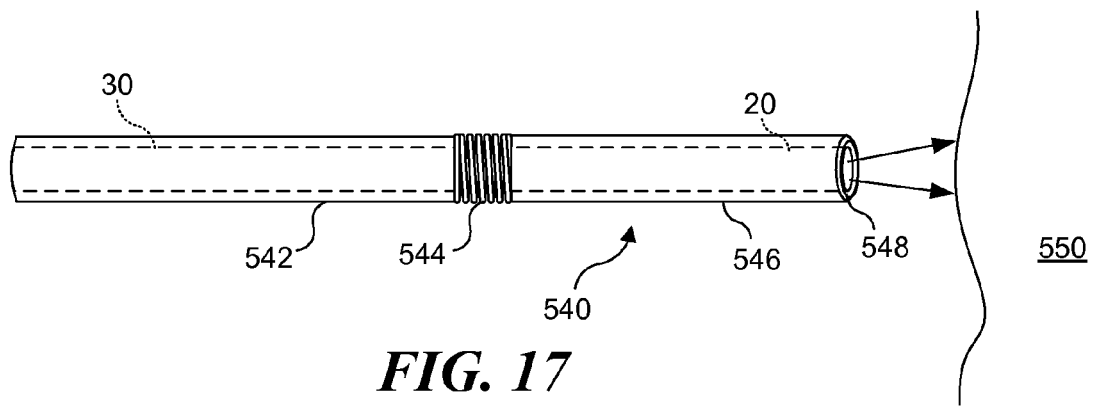
Figure 18:
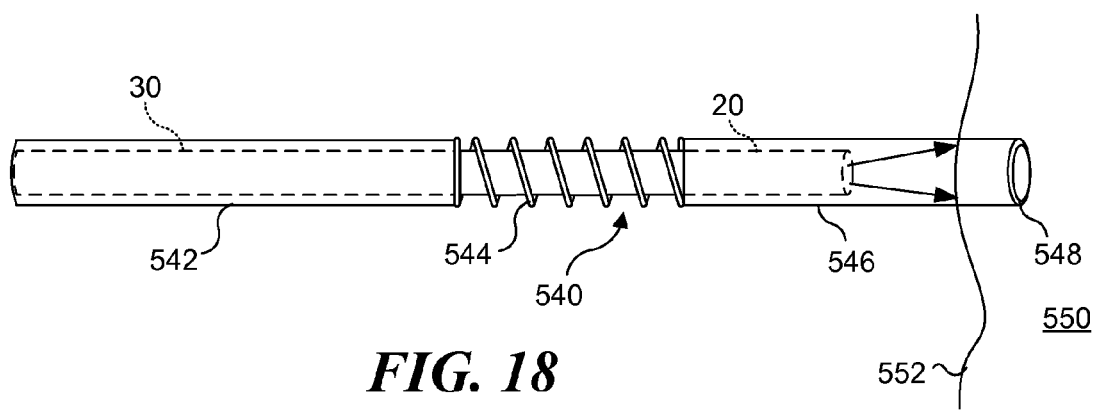

An exemplary embodiment of a cannula tool 540 that uses a different approach for taking a biopsy sample with a bevel needle end 548 is illustrated in FIGS. 17 and 18. FIG. 17 shows how a cannula tube 542 includes a compressed helical coil spring 544 that can be selectively released (for example, by pulling a trip lead that extends proximally inside cannula tube 542—not shown, or by applying an electrical signal to leads (not shown) that extend through inside the cannula tube to an electrically actuated trigger (also not shown)). The cannula tube and scanning fiber endoscope would be advanced with the helical spring pre-compressed, until imaging by the scanning fiber endoscope indicates that it is disposed adjacent a site 550 where it is appropriate to take a biopsy sample of cells and tissue. Cannula tube 542 is constrained with scanning fiber endoscope 20 when the helical spring is selectively released so that expansion of compressed helical spring 544 acts on a tubular segment 546 of the cannula tool, forcing it forward of the distal end of scanning fiber endoscope 20, as shown in FIG. 18. The force of the expanding helical spring thus causes bevel needle end 548 on the distal end of tubular segment 546 to pierce tissue at adjacent site 550, enabling cells and tissue to be freed from the site and withdrawn as a biopsy sample when cannula tube 542, tubular segment 546, and scanning fiber endoscope 20 are withdrawn from the patient's body.

Unless the biopsy sample is carried by a fluid through the annular gap between the interior surface of the cannula tube and the exterior surface of the scanning fiber endoscope, as explained in regard to some of the exemplary embodiments, it may be important to ensure that cells and tissue are retained by the bevel needle end that pierces tissue at a desired site, so that the cells and tissue are not lost as the bevel needle end is withdrawn from the patient's body. FIGS. 19, 20, and 21 illustrate different exemplary embodiments for anchoring the cannula tool to tissue, for example, to stabilize the cannula tool and the scanning fiber endoscope while carrying out high-resolution imaging or slow-imaging or to minimize the effects of respiration motion or other biological motion while imaging. In addition, these different embodiments can ensure that tissue and cells usable as a biopsy sample are retained by the bevel needle end when it is withdrawn from the tissue at an internal site. FIG. 19 shows a plurality of barbs 566, which are formed just inside a bevel needle edge 564 of a cannula tool 560. Barbs 566 can engage tissue and tear it away when a cannula tube 562 is rotated so that the barbs on the inside of the bevel needle end are turned into the tissue pierced by the bevel needle edge, at the internal site. Cells and tissue trapped by barbs 566 can then be collected after cannula tool 560 is withdrawn, or optionally, can be flushed free of the barbs and drawn with a bodily fluid or an introduced fluid into an annular gap 568, which is formed between the inner surface of cannula tool 562 and the outer surface of scanning fiber endoscope 20 and collected at the proximal end of cannula tube 562.

In FIG. 20, backward angled teeth 576 formed just inside the distal end of a cannula tool 570 can also tear away cells and tissue from an internal site as the cannula tool is pulled back from a site pierced by a bevel needle edge 574. The cells and tissue torn away by backward angled teeth 576 will be retained behind the teeth and can be collected after the cannula tool is removed from the body, or optionally can be flushed into and withdrawn through an annular gap 578, carried by a bodily fluid or introduced fluid. Vacuum pump 128 (FIG. 5A) can pull the tissue and cells with the fluid to the proximal end of cannula tube 572, through the annular gap.

A portion of a set of angled barbs 582 on a cannula tool 580 are illustrated in FIG. 21. These angled barbs are configured in a helical array inside the opening formed by a bevel needle end 574, disposed at the distal end of a cannula tube 584. As the cannula tool is turned or rotated after bevel needle end 574 has pierced tissue, the angled barbs slice away tissue and retain it on the angled barbs so that the tissue can be removed from the patient's body and collected as a biopsy sample. Again, optionally, the biopsy sample can be drawn through an annular gap 578 with fluid and extracted from the proximal end of the cannula tube, as explained above.

Figure 22A:
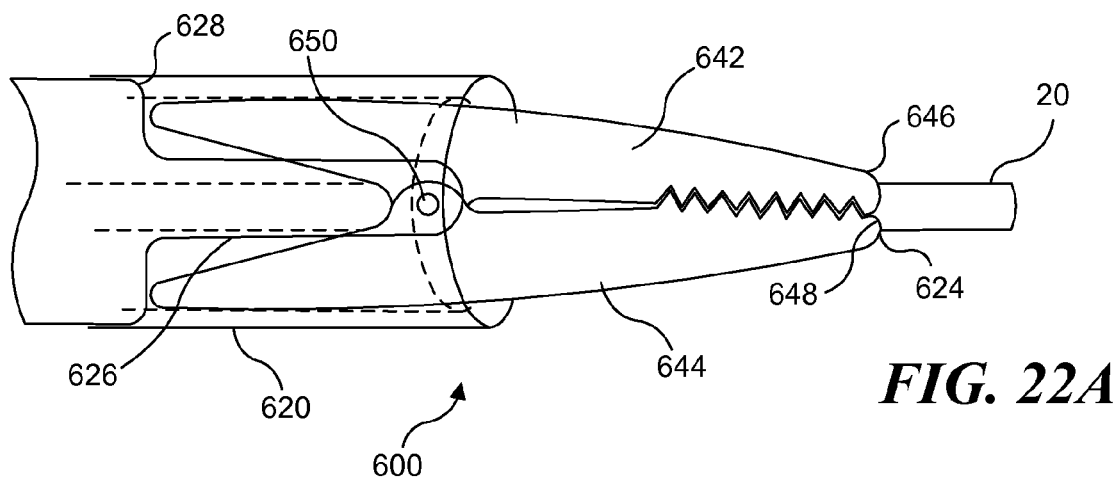
Figure 22B:
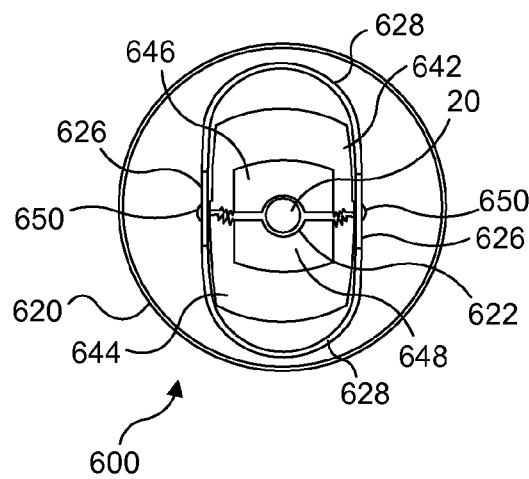
Figure 22C:
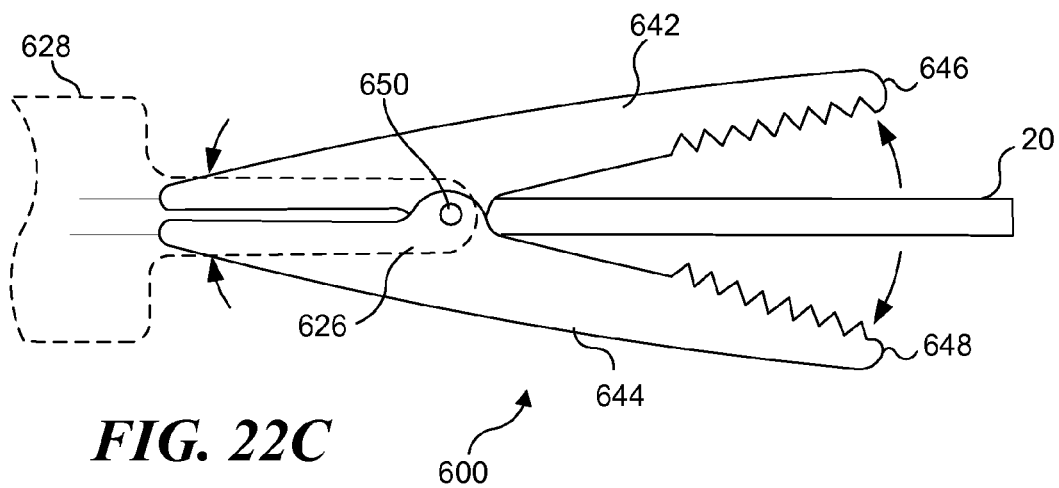
Figure 22D:
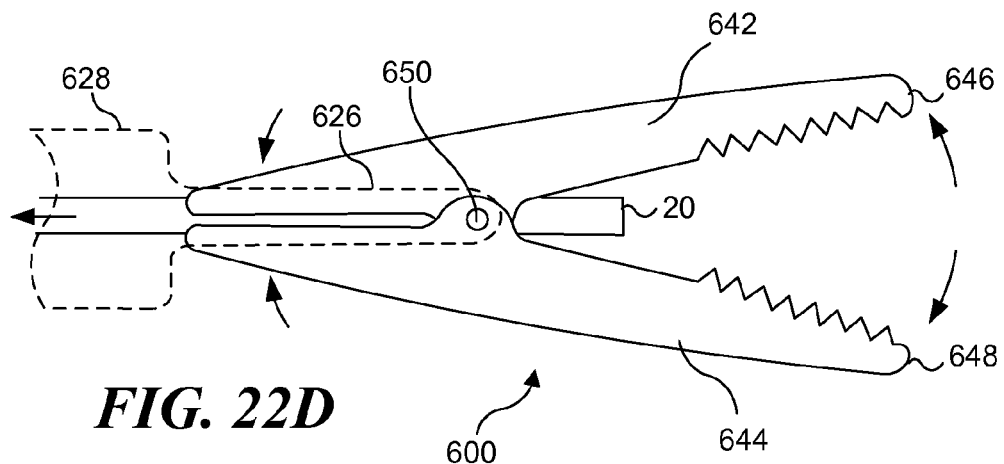
Figure 22E:
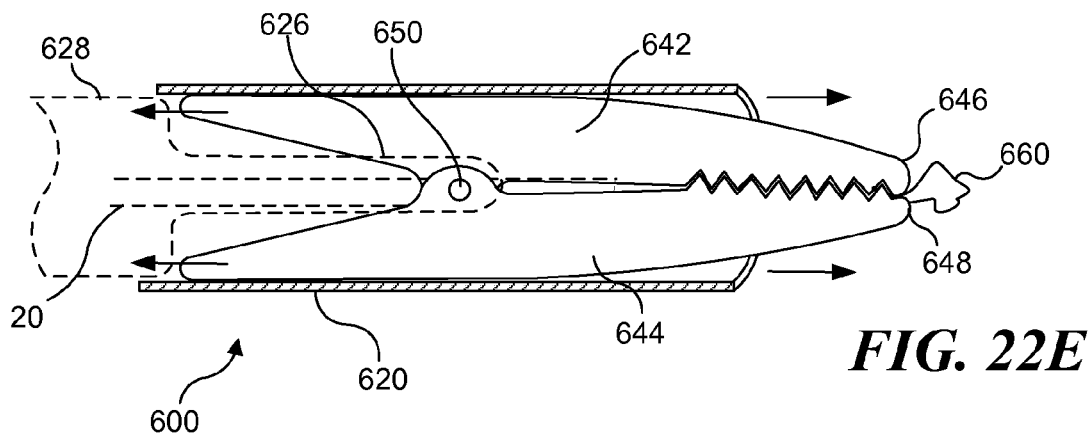

A forceps cannula tool can also be used to grasp tissue and remove a biopsy sample. An exemplary hollow head portion of forceps 600 is shown in FIG. 22A (side view) and FIG. 22B (distal end view). Other views of this exemplary embodiment are illustrated in FIGS. 22C, 22D, and 22E. Scanning fiber endoscope 20, which can be moved longitudinally relative to the hollow head portion of forceps 600, is shown passing through the center of the jaws of forceps 600 and out of a distal tip 624 of the jaws, via a channel 622 formed between an upper jaw 642 and a lower jaw 644 of the forceps, which are pivotally coupled together by hinge pins 650, which also attach to longitudinally extending arms 626, at each side of the forceps. An outer sheathing 620 encompasses the closed forceps to hold them closed and also provides a fluid communication path around the forceps through which fluid can flow into or from a body lumen in which the jaws of the forceps can be disposed. Longitudinally extending arms 626 are coupled to an internal tube 628 that extends externally from the proximal end of the system and is used to longitudinally push or pull forceps 600 so that the forceps move relative to outer sheathing 620 and/or scanning fiber endoscope 20. In this exemplary embodiment, both upper jaw 642 and lower jaw 644 can be biased open by a helical or other type of spring (not shown) or other suitable means, so that the distal ends of the jaws spread apart, as shown in FIG. 22C, when the jaws are extended beyond the outer sheathing or when the outer sheathing is drawn proximally relative to the forceps, so that the jaws are no longer encompassed by outer sheathing 620. In order to grasp tissue, the central scanning fiber endoscope is retracted relative to forceps 600, as shown in FIG. 22D. Once the forceps are closed, for example by advancing outer sheathing 620 over the jaws (thereby causing the jaws of the forceps to grasp and thereby remove a biopsy sample 660 of tissue from a site in a patient's body), the forceps and scanning fiber endoscope can be withdrawn from the patient's body together, with the outer sheath sheathing. The outer sheathing extends over the forceps when the forceps and biopsy sample are being withdrawn, as shown in FIG. 22E, to protect the biopsy sample and retain the jaws closed and grasping the biopsy sample.

In an alternative exemplary embodiment, a forceps 670, the jaws of the forceps can be configured so that they extend parallel with scanning fiber endoscope 20, as shown in FIG. 23. A lower jaw 684 of the forceps is rigidly attached to a flexible tubular conduit 680 that is sized and configured to readily slide over scanning fiber endoscope 20, which thus can be used as a guidewire to guide forceps 670 to a desired site in a patient's body. An upper jaw 682 can be opened with a draw wire 672 or by using an actuator (not shown), for example, an actuator that is formed of a shape memory metal such as Nitinol™, which changes shape in response to resistive heating caused by an electrical current supplied to the actuator through electrical leads (also not shown). Upper jaw 682 can be then closed toward lower jaw 684 by a further shape change of the actuator or by a helical or other type of spring (not shown) disposed at a hinge 686, so that the jaws grasp tissue for taking a biopsy sample. (It should be apparent that the relative operation and function of the upper and lower jaws can alternatively be reversed.) The biopsy sample can be taken from an internal site in a patient's body while imaging the site with scanning fiber endoscope 20, and the images can assist a medical practitioner in identifying the desired site and the tissue to be retrieved as the biopsy sample.

Figure 24A:
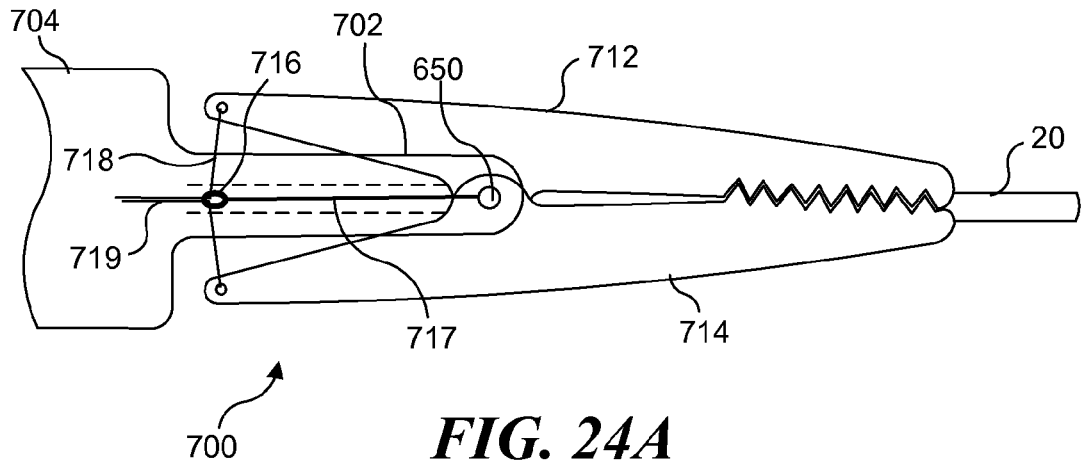
Figure 24B:
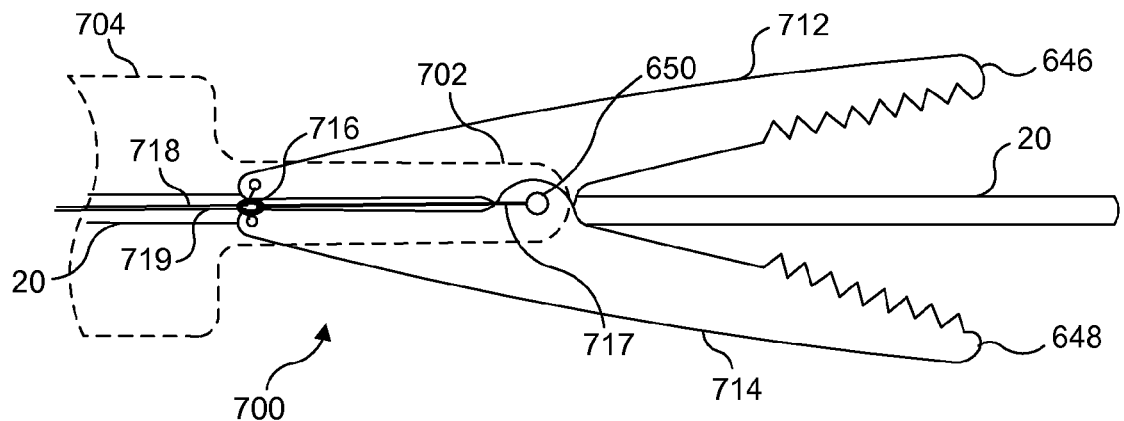

Several other exemplary mechanisms for opening and closing the jaws of the forceps tools are illustrated in FIGS. 24A through 24E. The simplest method is to provide very thin wires that pull the two rearwardly extending ends of jaws 712 and 714 together, as shown for an exemplary embodiment of forceps 700 in FIG. 24A. For example, wires 718 and 719 are coupled to the rearwardly extending ends of jaws 712 and 714 and then pass through a wire loop 716 that is coupled by a wire 717 to hinge 650 that pivotally couples the jaws together. Longitudinally extending arms 702 are coupled to an internal tube 704 that extends externally from the proximal end of the system and is used to longitudinally push or pull forceps 700 so that the forceps move relative to scanning fiber endoscope 20. By using internal tube 704 to hold forceps 700 in place while pulling wires 718 and 719 proximally, serrated distal ends 646 and 648 of the jaws can be opened, as shown in FIG. 24B. Alternatively, wires (not shown) connected to jaws 712 and 714 can be formed of a shape memory alloy wire (e.g., such as wire formed from Nintinol™) that is activated by selectively resistively heating the wire with an electrical current (or other heat source) to change shape from a straight to a foreshortened state. In both mechanisms, a helical spring (not shown) can be used to force the jaws closed when the opening force provided by the shape memory alloy wires is released.

Figure 24C:
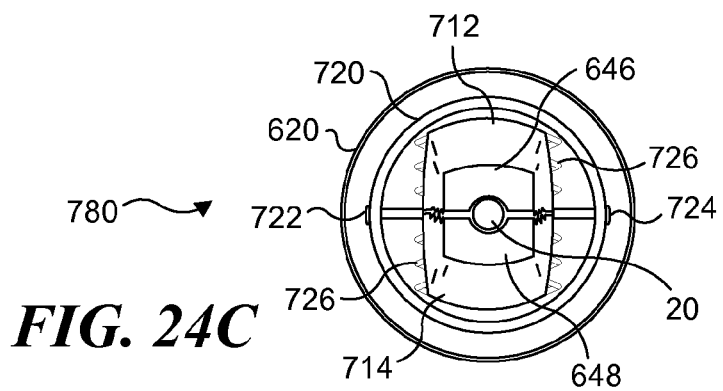
Figure 24D:
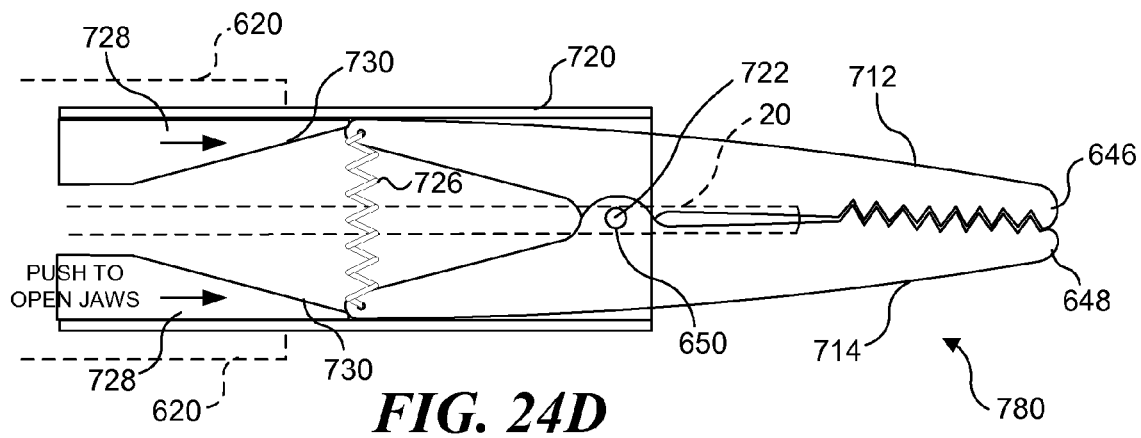
Figure 24E:
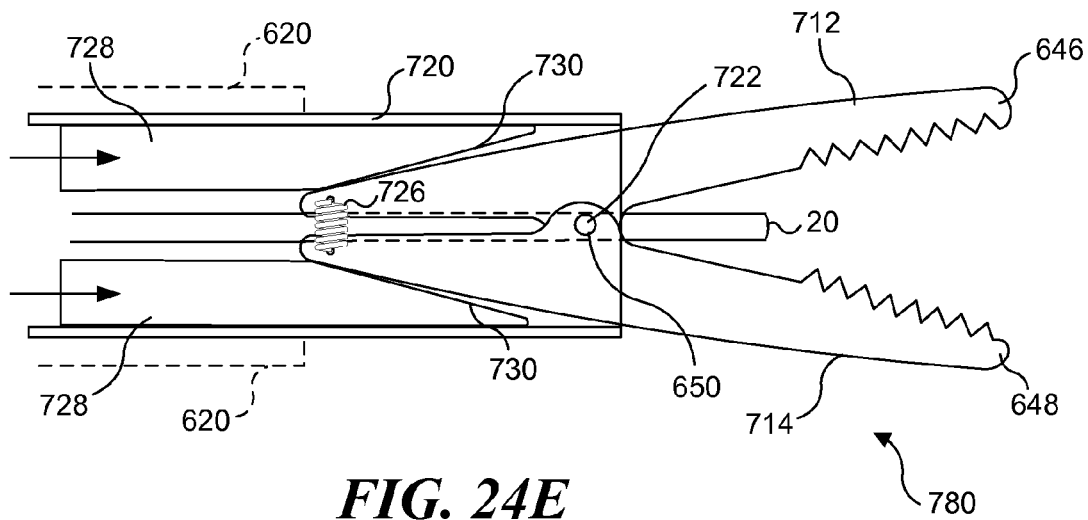

A third exemplary embodiment, a forceps 780 is shown in FIGS. 24C (distal end view), 24D (side phantom view with the jaws closed), and 24E (side view with the jaws open). In this embodiment, a cannula shaft 720 is shown attached to the forceps by pins 722 and 724 at hinge 650 where jaws 712 and 714 are pivotally coupled together. The jaws are opened by pushing an inner cannula 728 having angled ramp distal ends 730 forward against the rearwardly extending portions of the jaws, so that the angled ramp distal ends force the rearwardly extending ends of the jaws together, opening the distal ends of the jaws. The forceps are held stationary by simultaneously applying a restoring force on cannula shaft 720. Outer sheathing 620 can again optionally be used for providing fluid communication around forceps 780. When the inner cannula is pushed forward, a helical spring 726 disposed on the proximal end of the forceps jaws is compressed, as illustrated in FIG. 24E. Helical spring 726 supplies the force necessary to close the distal serrated ends of the jaws when the inner cannula is retracted away from the jaws so that it no longer applies force to the rearwardly extending portions of the jaws. Alternative configurations can be used for actuating the jaws, such as forcing the jaws closed with the inner cannula and providing a spring to open the jaws, and those skilled in the art of forceps design and manufacture will readily understand how these and other mechanisms can be employed to open/ close the jaws of the forceps.

Yet another exemplary embodiment of a cannula tool is illustrated in FIG. 25. A cannula tool 740 shown in this Figure is intended to cut away a ribbon of tissue with a sharpened cutting edge 744, which is formed over at least a portion of the distal leading edge of the elongate flexible tube. Unlike the other exemplary embodiments of cannula tools discussed above, cannula tool 740 has a flexible elongate tube 742 with an internal lumen 746 that does not slide over scanning fiber endoscope 20. Lumen 746 instead defines a passage through which a ribbon of tissue that is cut away by sharpened cutting edge 744 from adjacent tissue within the body of a patient can be drawn with bodily fluid toward the proximal end of the elongate flexible tube. While not shown in this Figure, it is contemplated that a protective cover can be provided that overlies sharpened cutting edge 744 until the distal end of the cannula tool is disposed where it is desired to cut away a ribbon of tissue as a biopsy sample. A pull wire (not shown) that is coupled to the protective cover can then be pulled proximally, enabling the protective cover to be pulled away from the sharpened cutting edge and out through the proximal end of lumen 746. Alternatively, during insertion and retraction, flexible elongate tube 742 can be rotated so that cutting edge 744 is disposed close to the guidewire and away from the tissue, then rotated outwardly toward the tissue, to cut away the biopsy sample.

The distal end of the cannula cutting tool is guided to a desired location by a piggyback collar 748, which is attached to one side of the flexible elongate tube with a stanchion 750. Piggyback collar 748 includes an internal open guide lumen that is sized to readily slide along scanning fiber endoscope 20, and thus, to be guided to a desired site within the body of a patient where a biopsy sample is to be taken. Stanchion 750 may enable elongate tube 742 to rotate but prevent it from sliding longitudinally to enable cutting edge 744 to be turned away from the tissue during insertion and retraction of the tool through the body lumen.

The simple cannula tool comprising annular gap 23 that is formed between the outer surface of scanning fiber endoscope and the inner surface of cannula tube 22, as shown in FIG. 2A, can be employed to assist in collecting a biopsy sample comprising cells that are released from tissue. The cells are released from the tissue as a result of an explosive thermal heating caused by a focused laser light that is emitted by the scanning fiber endoscope, as shown in regard to an exemplary embodiment 800 illustrated in FIG. 26. In this embodiment, cannula tube 22 is advanced over scanning fiber endoscope 20 within a body lumen 802 that is defined by walls 804. At an internal site 810, the scanning fiber endoscope is used to emit pulses of laser light 808 that are focused on the internal site where a biopsy sample is to be taken. The laser pulses cause rapid heating, disrupting the cells and tissue at the internal site so that cells 812 are freed and can be drawn with bodily fluid or by introduced fluid into annular gap 23 by vacuum pump 128 (FIG. 5A) and collected at the proximal end of the cannula tube.

Each of the exemplary embodiments of cannula tools discussed above is characterized by performing at least two functions. The first function is to dislodge or cutaway cells or tissue from within the body of a patient. The second function is to enable the cells or tissue that have been dislodged to be collected as a biopsy sample for further processing or analysis. A multi-functional capability and relatively compact size of these cannula tools enable them to be readily used in many applications where conventional cannula tools cannot be.

Fabricating the Cannula Tool System

The cannula tube is a hollow tube that slips over the sub-mm scanning fiber endoscope. Based on experience threading a 1.6 mm OD sheathing with 12 plastic optical fibers around a 1 mm diameter optical fiber scanner, the material surface properties of the contacting plastics must be controlled to reduce friction. In one exemplary embodiment, the outer sheathing of the sub-mm scanning fiber endoscope is fabricated of slick polyethylene plastic (e.g., having a coefficient of friction<0.3), and the inner surface of the cannula tube is formed of PolyTetraFluoroEthylene (PTFE—sold under the mark TEFLON™) coated polyurethane plastic. If necessary, an annular gap of about 0.2 mm can be maintained with small TEFLON™ standoff fins (not shown) adhered to the outside of the pre-assembled scanning fiber endoscope, reducing the area of contact and friction. The standoff fins formed from loops of plastic are expected to be attached to the scanning fiber endoscope by a friction fit.

At a proximal end, a water-tight seal between the interior surface of the cannula tube and the outer surface of the scanning fiber endoscope can be achieved by applying saline under pressure, as well as by removal of fluids by suction. Difficulties in extending the cannula beyond the scanning fiber endoscope may occur when the cannula is bent, either temporarily by the bending mechanism discussed above, or permanently, when using a bent-tip endoscope design. These difficulties can be minimized by maintaining the distal end of the cannula tool nearly flush with the distal end face of the scanning fiber endoscope during all image-guided cell sampling. A practical difficulty is that the saline used for lavage will cover the distal end of the scanning fiber endoscope lenses. Since the distal surface of the objective lens can be designed for both air and saline media, the forward-view (or side-view) image should not be distorted unless water droplets or bubbles are within the field of view. Previous scanning fiber endoscope lens designs optimized for air immersion have modeled the scanning fiber endoscope when immersed in saline, and the optimum focal length shifts slightly, but there is no apparent distortion in the scanning fiber endoscope image because of the long working distance objective lens assembly that has been provided for use in this exemplary embodiment by PENTAX Corporation. The annular gap in the cannula tools will be used to control the air/saline medium for immersion.

The cannula brush is a hollow tube constructed in a manner similar to the cannula for lavage except that the cannula brush includes short radial bristles at the distal tip for abrading the bronchiole lumen. At the proximal end of the cannula brush, there is an option for the lavage handling equipment since a lavage may be employed after brushing to insure that a sufficient quantity and quality of cells are collected. Since brushing captures cells within the bristles, the brush is likely to be a single-use device. A second site for cell sampling within a subject will require removal of the first cannula brush and insertion of a new, second cannula brush. Therefore, up to 10 cannula brushes will be fabricated once the optimal design is determined through consultations with the clinical collaborators.

The cannula tool for needle biopsy (like that shown in FIG. 2C) will be the most novel tool for the clinicians since the bore size will be greater than standard needles used for fine needle aspirates (FNA) and core biopsies. The needle is required for sampling cells that are not exposed on the lumens inner surface. Since the distal tip of the scanning fiber endoscope is rigid for about 12 mm in one exemplary embodiment, the rigid needle stock can be this long without affecting the scanning fiber endoscope navigation. One difficulty can arise when extending the needle past the scanning fiber endoscope and into tissue. An induced cough may be required during the procedure, which is often used for assisting the penetration of needles for minimally-invasive FNA sampling in humans. In addition, threaded outer needle stock may be tested in vivo. Another difficulty can arise when extracting the needle with a tissue sample, which can be assisted by applying suction to the needle at the proximal end or by twisting a customized needle having small barbs. Due to the unique scanned light illumination of the scanning fiber endoscope, the bronchial tissue can be observed much further down the peripheral airways than current bronchoscopes that use more diffuse illumination. Thus, as in the case of cannula tools for lavage and brushing, the image of the distal tissue surface will stay in focus as the needle is advanced over the guidewire-with-eyes toward the tissue, although the field of view will be greatly reduced. Although the bore size is greater than standard needles, it is expected that the ability to perform biopsy under direct vision will reduce the incidence of pneumothorax.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A catheter system with an imaging capability, for guiding a tool to a desired location within a body of a patient, the system comprising:
   (a) an elongate flexible catheter guide shaft having a proximal end and a distal end, said elongate flexible catheter guide shaft being adapted to be advanced within a body of a patient, to a desired location;
   (b) an optical imaging scanner having an outer diameter of 1.3 millimeters or less and configured to generate image data for providing at least two-dimensional optical imaging within a body of a patient, the optical imaging scanner having a scanning optical fiber configured to vibrate in a desired pattern so as to produce a variable field of view and the optical imaging scanner being disposed within and at the distal end of the elongate flexible guide shaft, the optical imaging scanner positioned within the elongate flexible catheter guide shaft so as to enable imaging directly forward along a longitudinal axis of the elongate flexible catheter guide shaft, both while the elongate flexible guide shaft is moving and while it is fixed in position, the optical imaging occurring at least during one of:
      (i) while the elongate flexible catheter guide shaft is being advanced within the body of a patient;
      (ii) while the distal end of the elongate flexible catheter guide shaft is disposed at a desired location within a body of a patient, the imaging scanner then imaging the tool in relationship with adjacent tissue, to enable optically viewing an interaction of the tool with the adjacent tissue, even if the tool has been advanced distally beyond a distal end of the elongate flexible catheter shaft; or
      (iii) while the elongate flexible catheter guide shaft is being withdrawn from within the body of a patient; and
   (c) a cannula that includes a lumen sized and shaped to readily form an annular gap with and slide over the elongate flexible catheter guide shaft toward the distal end of the elongate flexible guide shaft, the cannula having a diameter larger than a diameter of the elongate flexible catheter guide shaft and being adapted to be slid over and beyond the distal end of the elongate flexible catheter guide shaft and toward the desired location, the elongate flexible catheter shaft thus serving as a guidewire for positioning the cannula at the desired location within the body of a patient, wherein the diameter of the cannula is within the variable field of view of the scanner.

2. The catheter system of claim 1, wherein the cannula is sized sufficiently larger than the elongate flexible catheter guide shaft to provide a generally annular passage around an outer perimeter of the elongate flexible guide shaft, so that the annular passage is adapted to convey a lavage fluid for collecting cells from a desired location within a body of a patient.

3. The catheter system of claim 2, further comprising a pump in fluid communication with the annular passage, said pump being configured for extracting cells comprising a biopsy sample through the annular passage from a distal end of the cannula by drawing the biopsy sample with a fluid through the lumen, toward the proximal end of the elongate flexible catheter guide shaft.

4. The catheter system of claim 3, wherein when the cannula is disposed proximate to tissue, the pump applies a negative pressure that draws the tissue and the cannula toward each other.

5. The catheter system of claim 3, wherein the cannula includes a plurality of outwardly extending abrasive points disposed at spaced-apart positions on the exterior surface of the cannula, proximate to a distal end thereof, said abrasive points abrading cells from an internal site within a body of a patient for collection as a biopsy sample.

6. The catheter system of claim 5, further comprising a plurality of orifices formed in the cannula proximate to the spaced-apart positions where the plurality of outwardly extending abrasive points are disposed, so that the plurality of orifices provide fluid communication paths for cells conveyed with a fluid to pass into the annular passage and be drawn by the pump through the annular passage toward the proximal end of the cannula.

7. The catheter system of claim 3, further comprising a biopsy trap disposed between and in fluid communication with the pump and the proximal end of the cannula, the biopsy trap serving to trap cells and tissue comprising a biopsy sample after the biopsy sample exits from the cannula.

8. The catheter system of claim 3, wherein the cannula includes a balloon that is disposed around an exterior of the cannula adjacent to the distal end of the cannula, an outer surface of the balloon having an abrasive coating so that when the balloon is selectively inflated while the distal end of the cannula is disposed at an internal site within a body of a patient, and the cannula is moved while the abrasive coating is in contact with tissue at the internal site, cells are dislodged from the tissue by the abrasive coating on the balloon and are drawn with a fluid into and through the annular passage by the pump, toward the proximal end of the cannula.

9. The catheter system of claim 1, wherein the cannula includes a plurality of short bristles that extend outwardly of an outer surface of the cannula to provide a brush that dislodges cells and collects the cells dislodged from tissue at a desired location within a body of a patient.

10. The catheter system of claim 1, wherein the cannula has a sharpened distal end adapted to pierce tissue and collect cells dislodged from tissue at a desired location within a body of a patient.

11. The catheter system of claim 1, wherein the cannula comprises forceps that include jaws that can selectively be opened and closed, the jaws being configured so that when closed on tissue, the tissue can be withdrawn with the cannula as a biopsy sample, from an internal site within a body of a patient.

12. The catheter system of claim 1, wherein the cannula comprises a snare loop that extends generally distal of a distal end of the cannula, the snare loop being employed to cut away tissue comprising a biopsy sample from an internal site within a body of a patient.

13. The catheter system of claim 12, wherein the snare loop is coupled to a power supply that is selectively activated to heat the snare loop with an electrical current sufficiently to cut through tissue, thereby freeing the biopsy sample from adjacent tissue.

14. The catheter system of claim 12, wherein the snare loop is coupled to a line that extends proximally and is pulled to tighten the snare loop around tissue to cut the tissue from adjacent tissue.

15. The catheter system of claim 1, wherein the cannula tool includes a helical member having a cutting blade formed on its distal end and disposed in the cannula, within an annular gap defined between an interior surface of the cannula and an outer surface of the elongate flexible catheter guide shaft, rotation of the cannula causing the cutting blade to cut free a piece of tissue comprising a biopsy sample at an internal site within a body of a patient, the piece of tissue being then drawn into and through the annular gap toward a proximal end of the cannula.

16. The catheter system of claim 15, further comprising a prime mover, and a rotational driver that is configured to drivingly couple with the cannula where exposed outside a body of a patient, the prime mover causing the rotational driver to rotate the cannula about the elongate flexible catheter guide shaft so that the cutting blade is rotated into tissue to cut away the piece of tissue.

17. The catheter system of claim 1, further including a passage for conveying a pressurized fluid, wherein the passage is configured to direct the pressurized fluid at a velocity sufficient to dislodge cells from tissue at a desired location within a body of a patient, the cells that are dislodged being withdrawn through the passage when a suction at a subambient pressure is applied in fluid communication with a proximal end of the passage.

18. The catheter system of claim 1, wherein the cannula includes an outer elongate sheath that is movable between a first position that protects a tool portion of the cannula during insertion and retraction of the cannula within a body of a patient, and a second position that exposes the tool portion, when the tool portion is disposed at the desired internal site.

19. The catheter system of claim 1, wherein the cannula includes a guide collar disposed proximate to a distal end of the cannula, the guide collar being attached to one side of the cannula and having the lumen formed within the guide collar, the lumen being sized and configured to slide over the elongate flexible catheter guide shaft.

20. The catheter system of claim 3, wherein the annular passage serves to convey cells toward a proximal end of the cannula after the cells are released from tissue at a desired site as a result of an explosive thermal heating caused by a focused light beam transmitted from the imaging scanner toward the tissue.

21. A system for guiding a cannula that includes a tool, to a desired position within a body of a patient while imaging a path along which the system is being advanced or withdrawn, comprising:
(a) a flexible elongate catheter guide shaft to serve as a guidewire;
(b) an imaging device disposed at a distal end of the flexible elongate catheter guide shaft and having an outer diameter of 1.3 millimeters or less, the imaging device having a scanning optical fiber configured to vibrate in a desired pattern to produce a variable field of view and being adapted to scan while imaging, to produce an image signal corresponding to a two-dimensional image of tissue distally of the distal end of the flexible elongate catheter guide shaft and along a longitudinal axis of the elongate flexible catheter guide shaft, to image the path followed as the flexible elongate catheter guide shaft is introduced through a passage within a body of a patient, without requiring the imaging device to be rotated to produce the variable field of view, the imaging device enabling details of the path to be observed to assist introduction of the flexible elongate catheter guide shaft along the path, to the desired position within a body of a patient; and (c) a cannula having a lumen with a diameter and being sized to form an annular gap with the elongate flexible catheter guide shaft in order to slide freely along and beyond the distal end of the flexible elongate catheter guide shaft toward the desired position within the body of the patient, enabling the cannula to be guided by the flexible elongate catheter guide shaft when advanced to the desired position within the body of the patient or while the flexible elongate catheter is being withdrawn from the body of the patient, the imaging device optically imaging an interaction between the tool included with the cannula and tissue in the body of the patient, once the cannula is disposed at the desired position within the body of the patient, wherein the diameter of the lumen is within the variable field of view of the imaging device.

22. The system of claim 21, wherein the tool comprising the cannula includes means for freeing a biopsy sample from tissue at a desired position within a body of a patient, the biopsy sample comprising cells or a piece of the tissue.

23. The system of claim 22, wherein the cannula includes a passage for carrying the biopsy sample toward a proximal end of the passage, for collection external to a body of a patient.

24. The system of claim 21, further comprising a prime mover that applies a rotational force to the cannula to rotate the tool so that it interacts with tissue adjacent to the tool to free a biopsy sample from the tissue.

25. A system for guiding a tool to a desired location in a body of a patient, comprising:
(a) an elongate flexible catheter extending between a proximal end and a distal end to serve as a guidewire;
(b) a scanning fiber device having an outer diameter of 1.3 millimeters or less and comprising an optical fiber disposed at the distal end of the elongate flexible catheter guide shaft, said scanning fiber device having a variable field of view and including an actuator that vibrates the optical fiber in a desired pattern to scan a region in at least two dimensions, the scanning fiber device producing an output signal that is usable to produce an optical image of an internal site consisting of:
 (i) tissue and anatomical structures disposed distally of the distal end of the elongate flexible catheter guide shaft and directly forward, along a longitudinal axis of the elongate flexible catheter guide shaft while the elongate flexible catheter is being advanced along a path through a body of a patient, the optical image assisting in maneuvering the distal tip of the elongate flexible catheter guide shaft to a desired location; and
 (ii) tissue and anatomical structures after a distal tip of the elongate flexible catheter guide shaft has been advanced to a desired location within a body of a patient; and
(c) a cannula having a lumen, the lumen having a diameter sized to form an annular gap with the elongate flexible catheter guide shaft and being configured to be independently advanced over and beyond the distal end of the elongate flexible catheter and guided thereby to the desired location within the body of the patient to which the distal tip of the elongate flexible catheter has been advanced, such that a distal portion of the cannula extends beyond the distal end of the elongate flexible catheter guide shaft and the elongate flexible catheter guide shaft is configured so that the scanning fiber device can be disposed fully within the elongate flexible catheter guide shaft while scanning the tissue and anatomical structures at the desired location, to produce an optical image showing the tool interacting with the tissue at the desired location, wherein the diameter of the lumen is within the variable field of view of the scanning fiber device.

26. The system of claim 25, wherein the tool is adapted to free cells or a piece of tissue from a desired location within a body of a patient, the cells or the piece of tissue comprising a biopsy sample.

27. The system of claim 26, wherein the cannula includes a passage through which the biopsy sample is drawn toward a proximal end of the cannula, for collection.

28. The system of claim 27, further comprising:
(a) a pump for drawing the biopsy sample toward the proximal end of the cannula; and
(b) a trap disposed adjacent to the proximal end of the cannula, for collecting the biopsy sample.

29. The system of claim 26, further comprising a rotational driver for rotating the cannula and the tool, so that the tool interacts with adjacent tissue to free the biopsy sample from the adjacent tissue.

30. The system of claim 25, wherein the cannula includes a balloon disposed around an exterior surface of the cannula, adjacent to a distal end of the cannula, and a fluid passage through which a pressurized fluid is selectively communicated to an interior volume of the balloon to selectively inflate the balloon so that the balloon provides stabilization for the elongate flexible catheter guide shaft while imaging an internal site with the scanning fiber device.

31. The system of claim 25, wherein the tool includes a needle disposed at a distal end of the cannula that is selectively thrust into tissue, said needle being used to carry out at least one function selected from the group consisting of:
(a) stabilizing the elongate flexible catheter guide shaft while imaging with the scanning fiber device; and
(b) taking a biopsy sample from tissue at an internal site.

32. The system of claim 31, wherein the needle includes angled points disposed around a bevel edge of the needle that engage the tissue as the needle is thrust into the tissue.

33. The system of claim 26, wherein the tool comprises forceps having jaws that can be selectively closed to grasp tissue.

34. A system for guiding a tool to a desired location in a body of a patient, comprising:
(a) an elongate flexible catheter guide shaft extending between a proximal end and a distal end to serve as a guidewire;
(b) a resonant scanning beam device disposed at the distal end of the elongate flexible catheter guide shaft and having an outer diameter of 1.3 millimeters or less, said resonant scanning beam device configured to produce a variable field of view and including an actuator that vibrates a scanning optical fiber to move at about its resonant frequency and in a desired pattern, the resonant scanning beam device further including a sensor affixed to a distal face of a lens that is disposed at the distal end of the elongate flexible catheter guide shaft, the sensor configured to generate image data for producing an optical image of tissue in the region that is disposed longitudinally forward of the lens; and (c) a cannula having a lumen having a diameter sized to form an annular gap with the elongate flexible catheter guide shaft and being configured to be advanced over and beyond the distal end of the elongate flexible catheter guide shaft in order to be guided thereby to the desired location within the body of a patient to which the distal tip of the elongate flexible catheter guide shaft has been advanced, the resonant scanning beam device being capable of optically imaging tissue affected by the tool, while the resonant scanning beam device is disposed inside of the cannula and proximal of a distal end of the cannula, wherein the diameter of the cannula is within the variable field of view of the resonant scanning beam device.

35. The system of claim 34, wherein the cannula includes a tool for taking a biopsy sample comprising either cells or a piece of tissue from the desired location.

36. A system for carrying out an image-guided biopsy at a desired location in a body of a patient, comprising:
   (a) a flexible elongate catheter guide shaft having a distal end and a proximal end to serve as a guide wire, a cross-sectional diameter of the flexible elongate catheter guide shaft being less than 2 millimeters;
   (b) an optical imaging system disposed at the distal end of the flexible elongate catheter guide shaft and having an outer diameter of 1.3 millimeters or less, the imaging system having a scanning optical fiber configured to vibrate in a desired pattern so as to produce a variable field of view and the system being configured to produce a high resolution optical image of a site proximate to the distal end of the flexible elongate catheter guide shaft and including a region of the site that is distally directly forward of the distal end of the flexible elongate catheter guide shaft, along a longitudinal axis of the elongate flexible catheter guide shaft, by scanning the site in at least two dimensions, both while the flexible elongate catheter guide shaft is moving and while it is in a fixed position; and
   (c) a cannula having a lumen having a diameter sized to form an annular gap with the elongate flexible guide shaft and being shaped to slide freely over and beyond the distal end of the flexible elongate catheter guide shaft and to be guided by the flexible elongate catheter guide shaft toward a desired location in a body of a patient, the imaging system producing an optical image of tissue at a desired location to provide visual guidance for taking a biopsy sample of tissue at the desired location, the image visually showing a tool used for taking the biopsy sample and a spatial relationship between the tool and the tissue at the desired location, the image including the region that is distally and longitudinally forward of the distal end of the flexible elongate catheter guide shaft, wherein the diameter of the cannula is within the variable field of view of the optical imaging system.

37. The system of claim 36, wherein the cannula includes the tool for taking the biopsy sample.

38. The system of claim 37, wherein the tool comprises forceps having jaws with an opening formed therein through which the flexible elongate catheter guide shaft extends while the cannula is being guided toward the desired location, the elongate flexible catheter guide shaft being capable of being withdrawn proximally from the opening once the cannula is disposed at the desired location, to enable the jaws to be closed to selectively grasp tissue at the site.

* * * * *